(12) United States Patent
Stals et al.

(10) Patent No.: US 12,378,189 B2
(45) Date of Patent: *Aug. 5, 2025

(54) MULTI-AZIRIDINE COMPOUND

(71) Applicant: COVESTRO (NETHERLANDS) B.V., Geleen (NL)

(72) Inventors: Patrick Johannes Maria Stals, Geleen (NL); Daan Van Der Zwaag, Geleen (NL); Alfred Jean Paul Bückmann, Geleen (NL); Gerardus Cornelis Overbeek, Geleen (NL); Jan Van Riel, Geleen (NL)

(73) Assignee: Covestro (Netherlands) B.V., Geleen (NL)

( * ) Notice: Subject to any disclaimer, the term of this patent is extended or adjusted under 35 U.S.C. 154(b) by 602 days.

This patent is subject to a terminal disclaimer.

(21) Appl. No.: 17/791,860

(22) PCT Filed: Jan. 21, 2021

(86) PCT No.: PCT/EP2021/051389
§ 371 (c)(1),
(2) Date: Jul. 8, 2022

(87) PCT Pub. No.: WO2021/148567
PCT Pub. Date: Jul. 29, 2021

(65) Prior Publication Data
US 2023/0097706 A1 Mar. 30, 2023

(30) Foreign Application Priority Data

Jan. 22, 2020 (EP) ................... 20153154
Jan. 22, 2020 (EP) ................... 20153159
Jan. 22, 2020 (EP) ................... 20153239
Jan. 22, 2020 (EP) ................... 20153240
Jan. 22, 2020 (EP) ................... 20153242
Jan. 22, 2020 (EP) ................... 20153245
Jan. 22, 2020 (EP) ................... 20153246
Jan. 22, 2020 (EP) ................... 20153249
Jan. 22, 2020 (EP) ................... 20153250
Jan. 22, 2020 (EP) ................... 20153251
Jan. 22, 2020 (EP) ................... 20153253
Jan. 24, 2020 (EP) ................... 20153628
Jan. 24, 2020 (EP) ................... 20153630
Jul. 24, 2020 (EP) ................... 20187717

(51) Int. Cl.
*C07D 203/10* (2006.01)
*C07D 251/32* (2006.01)
(Continued)

(52) U.S. Cl.
CPC ......... *C07D 203/10* (2013.01); *C07D 251/32* (2013.01); *C07D 403/12* (2013.01); *C07D 403/14* (2013.01); *C07D 413/14* (2013.01); *C07D 487/14* (2013.01); *C08F 220/1804* (2020.02); *C08G 18/027* (2013.01); *C08G 18/0823* (2013.01); *C08G 18/0866* (2013.01); *C08G 18/12* (2013.01); *C08G 18/227* (2013.01); *C08G 18/246* (2013.01); *C08G 18/282* (2013.01); *C08G 18/2825* (2013.01); *C08G 18/283* (2013.01); *C08G 18/2865* (2013.01); *C08G 18/2875* (2013.01); *C08G 18/302* (2013.01); *C08G 18/3228* (2013.01);
(Continued)

(58) Field of Classification Search
CPC .. C07D 203/10; C07D 251/32; C07D 487/14; C08G 18/282; C08G 18/283
See application file for complete search history.

(56) References Cited

U.S. PATENT DOCUMENTS 3,329,674 A 7/1967 Bulbenko et al.
3,337,533 A 8/1967 Ham
(Continued)

FOREIGN PATENT DOCUMENTS

CN 1606574 A 4/2005
CN 1720223 A 1/2006
(Continued)

OTHER PUBLICATIONS

International Search Report for PCT/EP2021/051389 dated Apr. 28, 2021, 4 pages.
(Continued)

*Primary Examiner* — Heidi R Kelley
*Assistant Examiner* — Adam J Berro
(74) *Attorney, Agent, or Firm* — The Webb Law Firm

(57) ABSTRACT

The present invention relates to a multi-aziridine compound having: a) from 2 to 6 of the following structural units (A): whereby R', R" are as defined herein m is an integer from 1 to 6; b) one or more linking chains wherein each one of these linking chains links two of the structural units A; and c) a molecular weight in the range from 840 Daltons to 5000 Daltons. The multi-aziridine compound can be used for example for crosslinking of for example carboxylic acid functional polymers dissolved and/or dispersed in an aqueous medium.

(A)

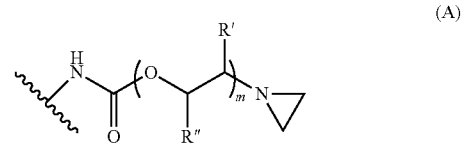

22 Claims, No Drawings

(51) Int. Cl.

| | | |
|---|---|---|
| C07D 403/12 | (2006.01) | |
| C07D 403/14 | (2006.01) | |
| C07D 413/14 | (2006.01) | |
| C07D 487/14 | (2006.01) | |
| C08F 220/18 | (2006.01) | |
| C08G 18/02 | (2006.01) | |
| C08G 18/08 | (2006.01) | |
| C08G 18/12 | (2006.01) | |
| C08G 18/22 | (2006.01) | |
| C08G 18/24 | (2006.01) | |
| C08G 18/28 | (2006.01) | |
| C08G 18/30 | (2006.01) | |
| C08G 18/32 | (2006.01) | |
| C08G 18/34 | (2006.01) | |
| C08G 18/38 | (2006.01) | |
| C08G 18/42 | (2006.01) | |
| C08G 18/44 | (2006.01) | |
| C08G 18/48 | (2006.01) | |
| C08G 18/66 | (2006.01) | |
| C08G 18/67 | (2006.01) | |
| C08G 18/73 | (2006.01) | |
| C08G 18/75 | (2006.01) | |
| C08G 18/76 | (2006.01) | |
| C08G 18/79 | (2006.01) | |
| C08G 18/83 | (2006.01) | |
| C08K 5/3412 | (2006.01) | |
| C08K 5/3492 | (2006.01) | |
| C08L 63/00 | (2006.01) | |
| C09D 7/20 | (2018.01) | |
| C09D 7/45 | (2018.01) | |
| C09D 7/63 | (2018.01) | |
| C09D 7/65 | (2018.01) | |
| C09D 11/101 | (2014.01) | |
| C09D 133/02 | (2006.01) | |
| C09D 133/04 | (2006.01) | |
| C09D 175/04 | (2006.01) | |
| C09D 175/08 | (2006.01) | |
| C09D 175/12 | (2006.01) | |

(52) U.S. Cl.
CPC ..... *C08G 18/3231* (2013.01); *C08G 18/3275* (2013.01); *C08G 18/348* (2013.01); *C08G 18/3842* (2013.01); *C08G 18/4291* (2013.01); *C08G 18/44* (2013.01); *C08G 18/4808* (2013.01); *C08G 18/4825* (2013.01); *C08G 18/4854* (2013.01); *C08G 18/4862* (2013.01); *C08G 18/4879* (2013.01); *C08G 18/6692* (2013.01); *C08G 18/6715* (2013.01); *C08G 18/73* (2013.01); *C08G 18/755* (2013.01); *C08G 18/758* (2013.01); *C08G 18/765* (2013.01); *C08G 18/792* (2013.01); *C08G 18/798* (2013.01); *C08G 18/833* (2013.01); *C08K 5/3412* (2013.01); *C08K 5/34924* (2013.01); *C08K 5/34926* (2013.01); *C08L 63/00* (2013.01); *C09D 7/20* (2018.01); *C09D 7/45* (2018.01); *C09D 7/63* (2018.01); *C09D 7/65* (2018.01); *C09D 11/101* (2014.01); *C09D 133/02* (2013.01); *C09D 133/04* (2013.01); *C09D 175/04* (2013.01); *C09D 175/08* (2013.01); *C09D 175/12* (2013.01); *C08G 2150/00* (2013.01)

(56) References Cited

U.S. PATENT DOCUMENTS

| | | | |
|---|---|---|---|
| 3,523,750 A | 8/1970 | Tesoro | |
| 3,560,415 A | 2/1971 | Grögler et al. | |
| 3,583,977 A | 6/1971 | Uelzmann | |
| 3,763,132 A | 10/1973 | Meiser | |
| 3,933,936 A | 1/1976 | Smith et al. | |
| 4,605,698 A | 8/1986 | Briden | |
| 5,106,993 A | 4/1992 | Kania | |
| 5,133,997 A | 7/1992 | Maier et al. | |
| 5,164,467 A | 11/1992 | Kania | |
| 5,241,001 A | 8/1993 | Kania et al. | |
| 5,258,481 A | 11/1993 | Hesselmans et al. | |
| 5,359,005 A | 10/1994 | Kania et al. | |
| 5,712,331 A | 1/1998 | Ryang | |
| 7,294,449 B1 | 11/2007 | Guideman et al. | |
| 7,396,891 B2 | 7/2008 | Gray et al. | |
| 8,318,855 B2 | 11/2012 | Schafheutle et al. | |
| 11,878,969 B2 * | 1/2024 | Overbeek | C09D 167/02 |
| 12,247,008 B2 * | 3/2025 | Stals | C09D 7/20 |
| 2003/0229176 A1 | 12/2003 | Trombetta et al. | |
| 2006/0117991 A1 | 6/2006 | Mayo et al. | |
| 2006/0148980 A1 | 7/2006 | Tielemans et al. | |
| 2007/0298006 A1 | 12/2007 | Tomalia et al. | |
| 2008/0114096 A1 | 5/2008 | Qu et al. | |
| 2010/0227945 A1 | 9/2010 | Bissinger et al. | |
| 2011/0086180 A1 | 4/2011 | Tielemans | |
| 2015/0118501 A1 | 4/2015 | Lu et al. | |
| 2017/0218110 A1 | 8/2017 | Arzt et al. | |

FOREIGN PATENT DOCUMENTS

| | | |
|---|---|---|
| CN | 1823110 A | 8/2006 |
| CN | 101365688 A | 2/2009 |
| CN | 101619164 A | 1/2010 |
| CN | 102046688 A | 5/2011 |
| CN | 104080861 A | 10/2014 |
| CN | 104379618 A | 2/2015 |
| CN | 105143297 A | 12/2015 |
| CN | 105377918 A | 3/2016 |
| CN | 105705598 A | 6/2016 |
| CN | 107922762 A | 4/2018 |
| CN | 108084870 | 5/2018 |
| CN | 110023354 A | 7/2019 |
| CN | 110248977 A | 9/2019 |
| CN | 110607120 A | 12/2019 |
| CN | 112469755 A | 3/2021 |
| CN | 117015566 A | 11/2023 |
| CN | 117836343 A | 4/2024 |
| EP | 0 507 407 | 10/1992 |
| EP | 0 758 662 | 2/1997 |
| EP | 1 865 014 | 12/2007 |
| GB | 1344725 | 1/1974 |
| JP | 47-027971 | 8/1972 |
| JP | 51-141860 | 5/1976 |
| JP | 59-128291 | 7/1984 |
| KR | 1020060066442 A | 6/2006 |
| WO | 2006/115547 | 11/2006 |
| WO | 2008069298 A1 | 6/2008 |
| WO | 2013/089927 | 6/2013 |
| WO | 2015/066868 | 5/2015 |
| WO | 2017216767 A1 | 12/2017 |
| WO | 2020/020714 | 1/2020 |

OTHER PUBLICATIONS

Written Opinion of the ISA for PCT/EP2021/051389 dated Apr. 28, 2021, 8 pages.

Dahlquist et al., "Contact allergy to trimethylolpropane triacrylate (TMPTA) in an aziridine plastic hardener", Contact Dermatitis, 1983, pp. 122-124, vol. 9.

Fei et al., "Properties and Curing Kinetic of Acrylic Resin Cured with Aziridine Crosslinker", Chinese Journal of Synthetic Chemistry, 2002, pp. 120-125, vol. 10, Issue 2.

(56) References Cited

OTHER PUBLICATIONS

Haitao et al., "Synthesis and Application of Aziridine Crosslinking Agent in Waterborne Coatings", Shanghai Coatings, 2013, 7 pages, vol. 51, No. 10.
Jiao, "Preparation of Waterborne Polyurethane Based on Renewable Resources and Its Film Properties", Masteral Dissertation, Dalian University of Technology, 2010, 79 pages.
Lee et al., "Preparation and characterization of acrylic pressure-sensitive adhesives based on UV and heat curing systems", International Journal of Adhesion and Adhesives, 2017, 21 pages.
Qingfang et al., "Study on heat resistance of polyurethane-imide/organosilicon modified epoxy coatings", Synthetic Materials and Applications, 2018, 5 pages, vol. 47, No. 3.
Walsh et al., "Polyamine-Functional Sterically Stabilized Latexes for Covalently Cross-Linkable Colloidosomes", Langmuir, 2010, pp. 18039-18048, vol. 26(23).
Wang et al., "Pervaporation Properties to Aromatic/Non-Aromatic Hydrocarbon Mixtures of Cross-Linked Membranes of Copoly(methacrylates) with Pendant Phosphate and Carbamoylphosphonate Groups", Journal of Membrane Science, 2002, pp. 13-27, vol. 199.
Yoo et al., "Preparation of Acrylic Copolymers and Crosslinking Agents and Properties as a Film", Journal of Applied Polymer Science, 2009, pp. 1587-1594, vol. 112.
Zilin et al., "Effect of Crosslinking Agent on Waterborne Polyurethane Wet Friction Fixing Agent", Shandon Chemical Industry, 2019, pp. 1-4, vol. 8, Issue 14.

* cited by examiner

MULTI-AZIRIDINE COMPOUND

This application is the U.S. national phase of International Application No. PCT/EP2021/051389 filed Jan. 21, 2021 which designated the U.S. and claims priority to EP patents application Nos. 20153154.8 filed Jan. 22, 2020, 20153159.7 filed Jan. 22, 2020, 20153239.7 filed Jan. 22, 2020, 20153240.5 filed Jan. 22, 2020, 20153242.1 filed Jan. 22, 2020, 20153245.4 filed Jan. 22, 2020, 20153246.2 filed Jan. 22, 2020, 20153249.6 filed Jan. 22, 2020, 20153250.4 filed Jan. 22, 2020, 20153251.2 filed Jan. 22, 2020, 20153253.8 filed Jan. 22, 2020, 20153628.1 filed Jan. 24, 2020, 20153630.7 filed Jan. 24, 2020, and 20187717.2 filed Jul. 24, 2020, the entire contents of each of which are hereby incorporated by reference.

The present invention relates to compounds with at least two aziridinyl groups which can be used for example for crosslinking of for example carboxylic acid functional polymers dissolved and/or dispersed in an aqueous medium.

Over the years, the need for coatings with improved resistances, like stain and solvent resistance, improved mechanical properties and improved adhesive strength is more and more growing. One or more of those properties can be elevated to a higher level by means of crosslinking. Many crosslink mechanisms have been studied over the years and for waterborne dispersions, the most useful ones include isocyanate crosslinking of hydroxyl functional dispersions, the reaction between carbodiimide and carboxylic acid, epoxy crosslinking and crosslinking using aziridine based crosslinkers.

U.S. Pat. No. 5,133,997 describes coating compositions comprising an aqueous dispersion of linear aliphatic urethane resins, an anionic surfactant and a crosslinking agent capable of facilitating the cure of said resin. Trimethylolpropane tris(2-methyl-1-aziridinepropionate), CAS number 64265-57-2, a polyfunctional aziridine crosslinker, is used as crosslinking agent, which is well-known and very active for crosslinking carboxylic acid functional polymers. This crosslinker however has an unfavourable genotoxic profile. US-A-2015118501 relates to anti-fog coating compositions comprising an aqueous polymeric dispersion and a crosslinker such as an aziridine crosslinker; in preparative example 4 a multi-functional aziridine crosslinker is prepared via Michael addition of ethoxylated trimethylolpropane triacrylate and 2-methylaziridine. U.S. Pat. No. 3,763,132 relates to curable compositions comprising carboxyl-containing polymers and aziridines such as the adduct of propylene imine and trimethylolpropane trimethacrylate useful as e.g. coating applications. There is a need in the industry to improve the safety, health and environmental profile of adhesives, inks and coatings and also of the substances used for preparing adhesives, inks and coatings. Genotoxicity describes the property of chemical or physical agents that cause any type of DNA damage, which may not always lead to a transmittable mutation. Mutagenicity refers to the induction of permanent transmissible DNA changes (as DNA composition or chromosome structure), which are retained in somatic cell division and passed onto progeny in germ cells. Genotoxicity must not be confused with mutagenicity. All mutagens are genotoxic whereas not all genotoxic substances are mutagenic.

The object of the present invention is to provide a compound with at least two aziridinyl groups which has reduced genotoxicity compared to trimethylolpropane tris (2-methyl-1-aziridinepropionate) and with good crosslinking efficiency. Compounds with at least two aziridinyl groups are further referred herein as multi-aziridine compounds.

This object has surprisingly been achieved by providing a multi-aziridine compound having:
a) from 2 to 6 of the following structural units (A):

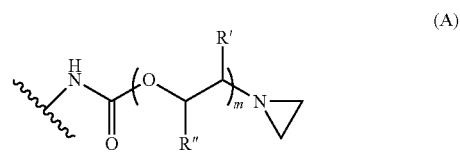

(A)

whereby
m is an integer from 1 to 6; and
R' and R" are according to (1) or (2):
(1) R'=H or an aliphatic hydrocarbon group containing from 1 to 14 carbon atoms, and
R"=H, an aliphatic hydrocarbon group containing from 1 to 14 carbon atoms, a cycloaliphatic hydrocarbon group containing from 5 to 12 carbon atoms, an aromatic hydrocarbon group containing from 6 to 12 carbon atoms, $CH_2$—O—(C=O)—R'", $CH_2$—O—R"", or $CH_2$—(OCR""HCR"" H)$_n$—OR""", whereby R'" is an aliphatic hydrocarbon group containing from 1 to 14 carbon atoms and R"" is an aliphatic hydrocarbon group containing from 1 to 14 carbon atoms or an aromatic hydrocarbon group containing from 6 to 12 carbon atoms, n being from 1 to 35, R"" independently being H or an aliphatic hydrocarbon group containing from 1 to 14 carbon atoms and R""" being an aliphatic hydrocarbon group containing from 1 to 4 carbon atoms, and
whereby either R' or R" is not H;
(2) R' and R" form together a saturated cycloaliphatic hydrocarbon group containing from 5 to 8 carbon atoms;
b) one or more linking chains wherein each one of these linking chains links two of the structural units A present in the multi-aziridine compound; and
c) a molecular weight in the range of from 840 Daltons to 5000 Daltons.

It has surprisingly been found that the multi-aziridine compounds according to the invention have reduced genotoxicity compared to trimethylolpropane tris(2-methyl-1-aziridinepropionate). The multi-aziridine compounds according to the invention show either only weakly positive induced genotoxicity or even they do not show genotoxicity, i.e. they show a genotoxicity level comparable with the naturally occurring background.

The genotoxicity can be measured by the ToxTracker® assay (Toxys, Leiden, the Netherlands) as further described herein. The ToxTracker® assay can be applied for pure substances or for compositions which are the direct products obtained in the preparation of the multi-aziridine compounds of the invention. With positive induced genotoxicity is meant that the induction level of the biomarkers Bscl2-GFP and Rtkn-GFP is equal to or higher than 2-fold at at least one of 10, 25 and 50% cytotoxicity in the absence or presence of the metabolizing system rat S9 liver extract. With weakly positive induced genotoxicity is meant that the induction level of the biomarkers Bscl2-GFP and Rtkn-GFP is higher than 1.5-fold and lower than 2-fold at at least one of 10, 25 and 50% cytotoxicity (but lower than 2-fold at 10, 25 and 50% cytotoxicity) in the absence or presence of rat S9 liver extract-based metabolizing systems (aroclor1254-induced rats, Moltox, Boone, NC, USA). With genotoxicity comparable with the naturally occurring background is meant that the induction level of the biomarkers Bscl2-GFP and Rtkn-GFP is less than or equal to 1.5-fold at 10, 25 and 50% cytotoxicity in the absence and presence of rat S9 liver extract-based metabolizing systems (aroclor1254-induced rats, Moltox, Boone, NC, USA). The induction level of the genotoxicity reporters Bscl2-GFP and Rtkn-GFP is preferably less than or equal to 1.5-fold at 10, 25 and 50% cytotoxicity in the absence and presence of rat S9 liver extract-based metabolizing systems (aroclor1254-induced rats, Moltox, Boone, NC, USA). A substance showing an induction level less than or equal to 1.5-fold at 10, 25 and 50% cytotoxicity in the absence and presence of rat S9 liver extract-based metabolizing systems (aroclor1254-induced rats, Moltox, Boone, NC, USA) is not genotoxic.

Crosslinking efficiency of a crosslinker can be assessed by assessing the chemical resistance defined and determined as described below.

For all upper and/or lower boundaries of any range given herein, the boundary value is included in the range given, unless specifically indicated otherwise. Thus, when saying from x to y, means including x and y and also all intermediate values.

The term "coating composition" encompasses, in the present description, paint, coating, varnish, adhesive and ink compositions, without this list being limiting. The term "aliphatic hydrocarbon group" refers to optionally branched alkyl, alkenyl and alkynyl group. The term "cycloaliphatic hydrocarbon group" refers to cycloalkyl and cycloalkenyl group optionally substituted with at least one aliphatic hydrocarbon group. The term "aromatic hydrocarbon group" refers to a benzene ring optionally substituted with at least one aliphatic hydrocarbon group. These optional aliphatic hydrocarbon group substituents are preferably alkyl groups. Examples of cycloaliphatic hydrocarbon groups with 7 carbon atoms are cycloheptyl and methyl substituted cyclohexyl. An example of an aromatic hydrocarbon group with 7 carbon atoms is methyl substituted phenyl. Examples of aromatic hydrocarbon groups with 8 carbon atoms are xylyl and ethyl substituted phenyl.

Whilst the structural units (A) present in the multi-aziridine compound according to the invention may independently have different R', R" and/or m, the structural units (A) present in the multi-aziridine compound are preferably identical to each other.

The multi-aziridine compound according to the invention is usually obtained in a composition in which, next to the multi-aziridine compound, remaining starting materials, side-products and/or solvent used in the preparation of the multi-aziridine compounds may be present. The composition may contain only one multi-aziridine compound according to the invention but may also contain more than one multi-aziridine compound according to the invention. Mixtures of multi-aziridine compounds are for example obtained when a mixture of polyisocyanates as starting material are used.

The urethane aziridine compound according to the invention contains from 2 to 6 of the structural units (A), preferably from 2 to 4 of the structural units (A), more preferably 2 or 3 structural units (A). m is an integer from 1 to 6, preferably m is from 1 to 4, more preferably m is 1 or 2 and most preferably m is 1.

Preferably, R' and R" are according to (1) or (2):
(1) R'=H or an alkyl group containing from 1 to 14 carbon atoms, preferably from 1 to 4 carbon atoms, more preferably from 1 to 2 carbon atoms, and R"=H, an aliphatic hydrocarbon group containing from 1 to 4 carbon atoms, $CH_2$—O—(C=O)—R''', $CH_2$—O—R'''', or $CH_2$—(OCR''''HCR''''H)$_n$—OR''''', whereby R''' is an alkyl group containing from 1 to 14 carbon atoms, preferably an alkyl group containing from 3 to 12 carbon atoms, more preferably a branched alkyl group with from 3 to 12 carbon atoms such as for example neopentyl or neodecyl, most preferably R''' is a branched C9 alkyl and R'''' is an alkyl group containing from 1 to 14 carbon atoms, such as for example ethyl, butyl, 2-ethylhexyl, n being from 1 to 35, preferably n being from 6 to 20, R'''''' independently being H or a methyl group and R'''''' being an alkyl group containing from 1 to 4 carbon atoms, and whereby either R' or R" is not H;
(2) R' and R" form part of a saturated cycloaliphatic hydrocarbon group containing from 5 to 8 carbon atoms.

More preferably R'=H and R"=an aliphatic hydrocarbon group containing from 1 to 14 carbon atoms, a cycloaliphatic hydrocarbon group containing from 5 to 12 carbon atoms, an aromatic hydrocarbon group containing from 6 to 12 carbon atoms, $CH_2$—O—(C=O)—R''', $CH_2$—O—R'''', or $CH_2$—(OCR''''HCR''''H)$_n$—OR''''', whereby R''' is an aliphatic hydrocarbon group containing from 1 to 14 carbon atoms and R'''' is an aliphatic hydrocarbon group containing from 1 to 14 carbon atoms or an aromatic hydrocarbon group containing from 6 to 12 carbon atoms, n being from 1 to 35, R'''''' independently being H or an aliphatic hydrocarbon group containing from 1 to 14 carbon atoms and R'''''' being an aliphatic hydrocarbon group containing from 1 to 4 carbon atoms. More preferably, R' is H and R"=an alkyl group containing from 1 to 4 carbon atoms, $CH_2$—O—(C=O)—R''', $CH_2$—O—R'''', or $CH_2$—(OCH$_2$CH$_2$)$_n$—OCH$_3$, whereby R''' is an alkyl group containing from 3 to 12 carbon atoms and R'''' is an alkyl group containing from 1 to 14 carbon atoms. More preferably, R' is H and R"=an alkyl group containing from 1 to 4 carbon atoms, $CH_2$—O—(C=O)—R''', $CH_2$—O—R'''', or $CH_2$—(OCH$_2$CH$_2$)$_n$—OCH$_3$ whereby R''' is preferably an alkyl group containing from 3 to 12 carbon atoms, more preferably a branched alkyl group with from 3 to 12 carbon atoms, such as for example neopentyl or neodecyl. Most preferably R''' is a branched C9 alkyl. R'''' is preferably an alkyl group containing from 2 to 14 carbon atoms. Non-limited examples for R'''' are butyl and 2-ethylhexyl.

The molecular weight of the multi-aziridine compound according to the invention is from 840 to 5000 Daltons. The molecular weight of the multi-aziridine compound according to the invention is preferably at most 3800 Daltons, more preferably at most 3600 Daltons, more preferably at most 3000 Daltons, more preferably at most 1600 Daltons, even more preferably at most 1400 Daltons. The molecular weight of the multi-aziridine compound according to the invention is preferably at least 890 Daltons, more preferably at least 940 Daltons and most preferably at least 1000

Daltons. As used herein, the molecular weight of the multi-aziridine compound is the calculated molecular weight. The calculated molecular weight is obtained by adding the atomic masses of all atoms present in the structural formula of the multi-aziridine compound. If the multi-aziridine compound is present in a composition comprising more than one multi-aziridine compound according to the invention, for example when one or more of the starting materials to prepare the multi-aziridine compound is a mixture, the molecular weight calculation can be performed for each compound individually present in the composition. The molecular weight of the multi-aziridine compound according to the invention can be measured using MALDI-TOF mass spectrometry as described in the experimental part below.

The multi-aziridine compound according to the invention comprises one or more linking chains wherein each one of these linking chains links two of the structural units A. The linking chains present in the multi-aziridine compound preferably consist of from 4 to 300 atoms, more preferably from 5 to 250, more preferably from 6 to 100 atoms and most preferably from 6 to 20 atoms. The atoms of the linking chains are preferably C and optionally N, O, S and/or P, preferably C and optionally N and/or O. The linking chains are preferably a collection of atoms covalently connected which collection of atoms consists of i) carbon atoms, ii) carbon and nitrogen atoms, or iii) carbon, oxygen and nitrogen atoms.

A linking chain is defined as the shortest chain of consecutive atoms that links two structural units A. The following drawing shows, for an example of a multi-aziridine compound according to the invention, the linking chain between two structural units A.

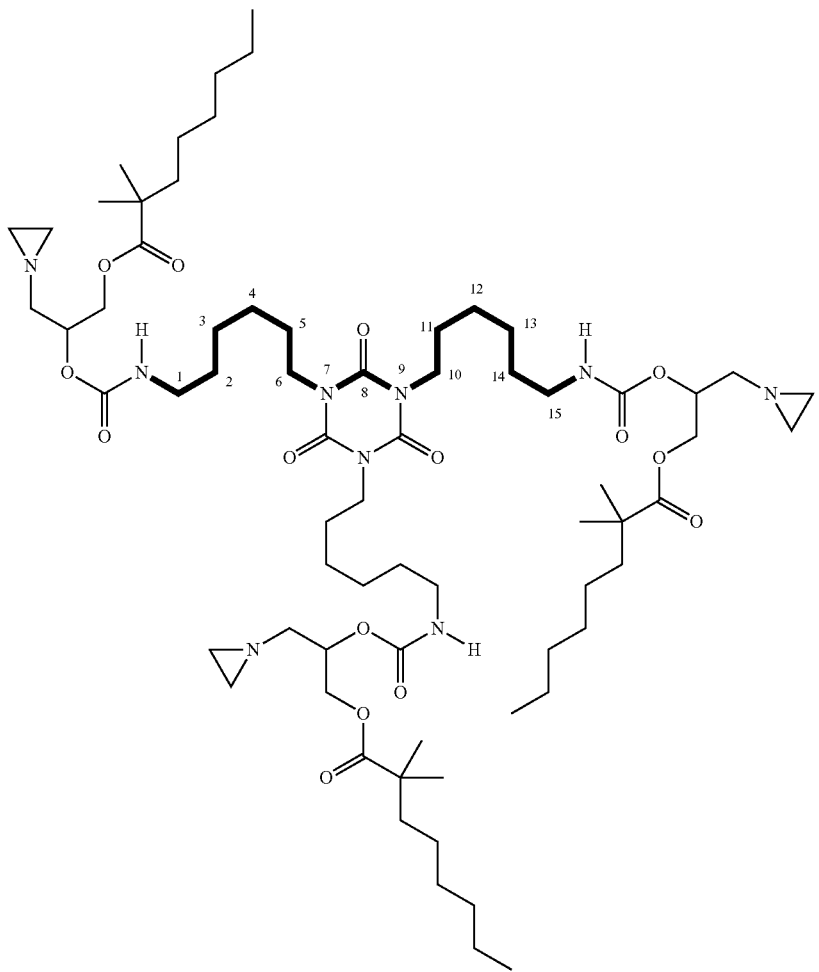

Any two of the structural units A present in the multi-aziridine compound of the invention are linked via a linking chain as defined herein. Accordingly, each structural unit A present in the multi-aziridine compound of the invention is linked to every other structural unit A via a linking chain as defined herein. In case the multi-aziridine compound according to the invention has two structural units A, the multi-aziridine compound has one such linking chain linking these two structural units. In case the multi-aziridine compound according to the invention has three structural units A, the multi-aziridine compound has three linking chains, whereby each of the three linking chains is linking a structural unit A with another structural unit A, i.e. a first structural unit A is linked with a second structural unit A via a linking chain and the first and second structural units A are both independently linked with a third structural unit A via their respective linking chains.

The following drawings show for an example of a multi-aziridine compound having three structural units A, the three linking chains whereby each one of the three linking chains links two structural units A.
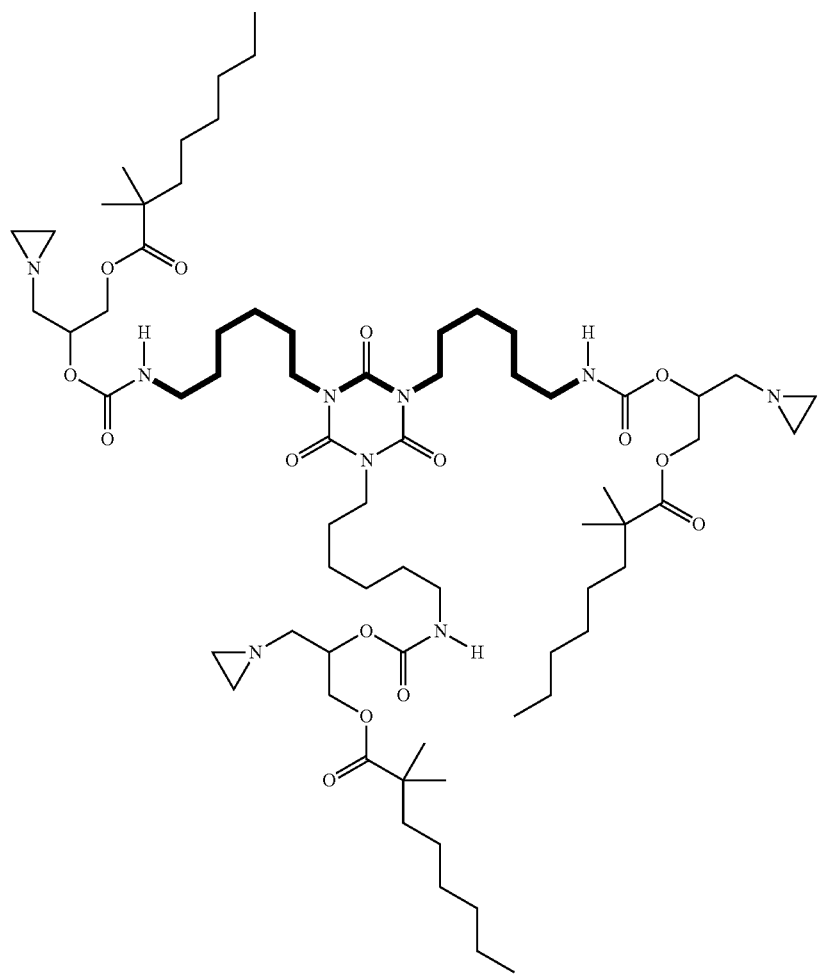

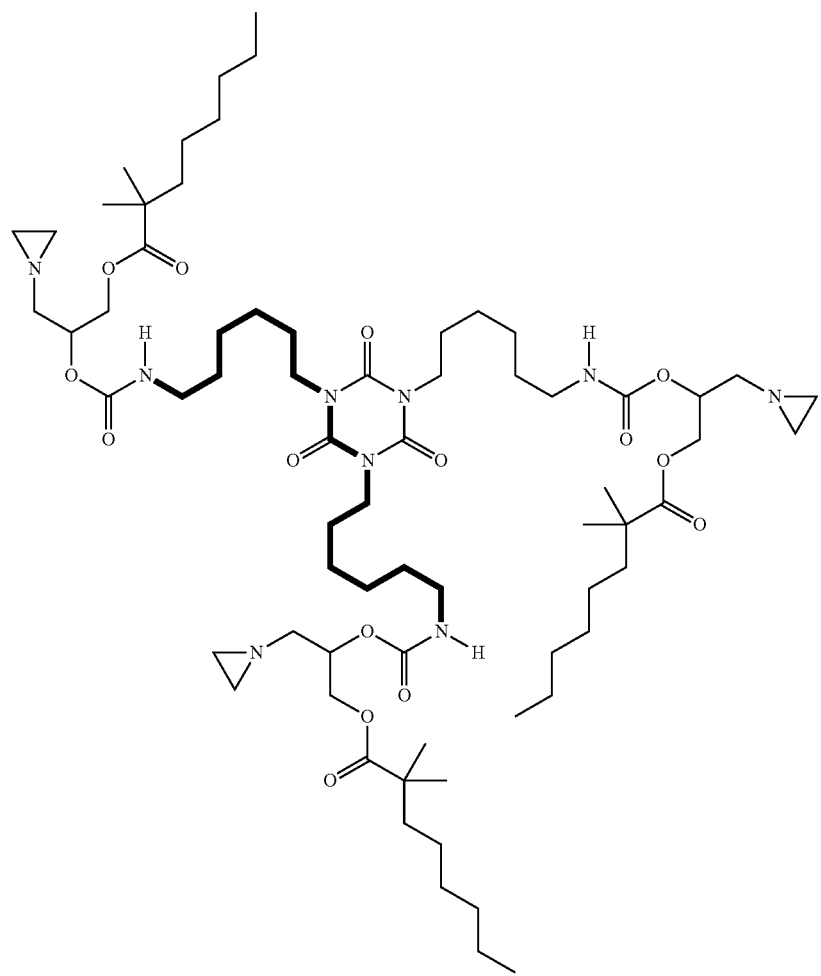

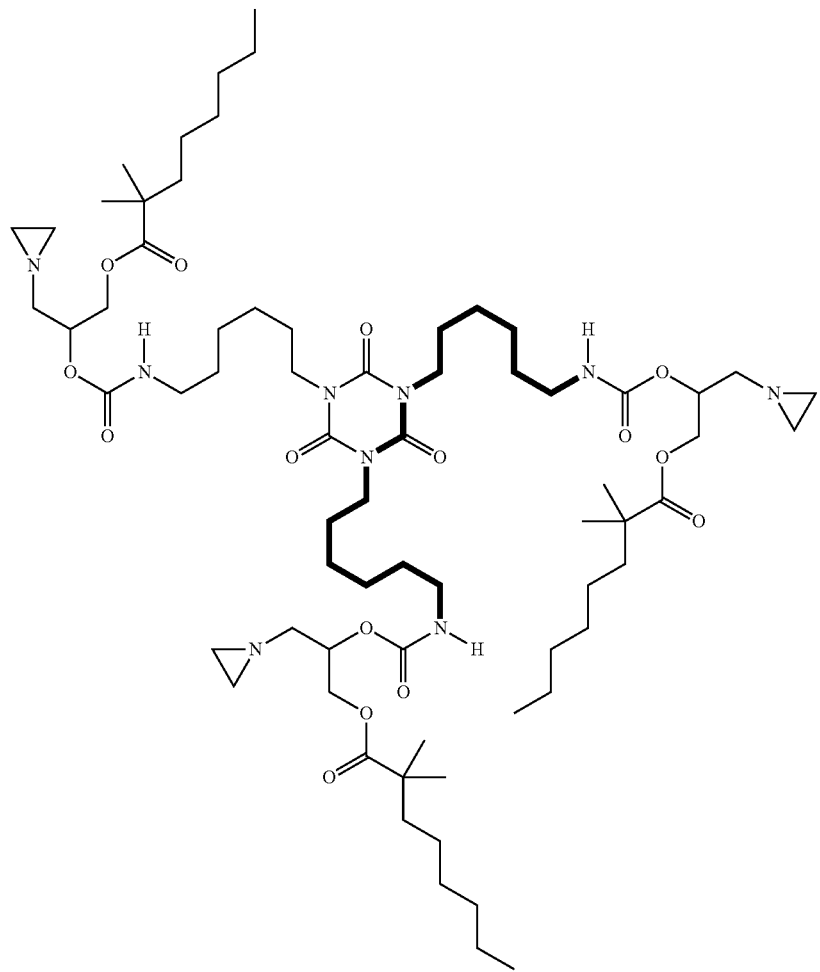

50

Multi-aziridine compounds according to the invention with more than two structural units A have a number of linking chains according to the following equation: LC={(AN−1)×AN}/2, whereby LC=the number of linking chains and AN=the number of structural units A in the multi-aziridine compound. So for example if there are 5 structural units A in the multi-aziridine compound, AN=5; which means that there are {(5−1)×5}/2=10 linking chains.

Preferably, the number of consecutive C atoms and optionally O atoms between the N atom of the urethane group in a structural unit A and the next N atom which is either present in the linking chain or which is the N atom of the urethane group of another structural unit A is at most 9, as shown in for example the following multi-aziridine compounds according to the invention.

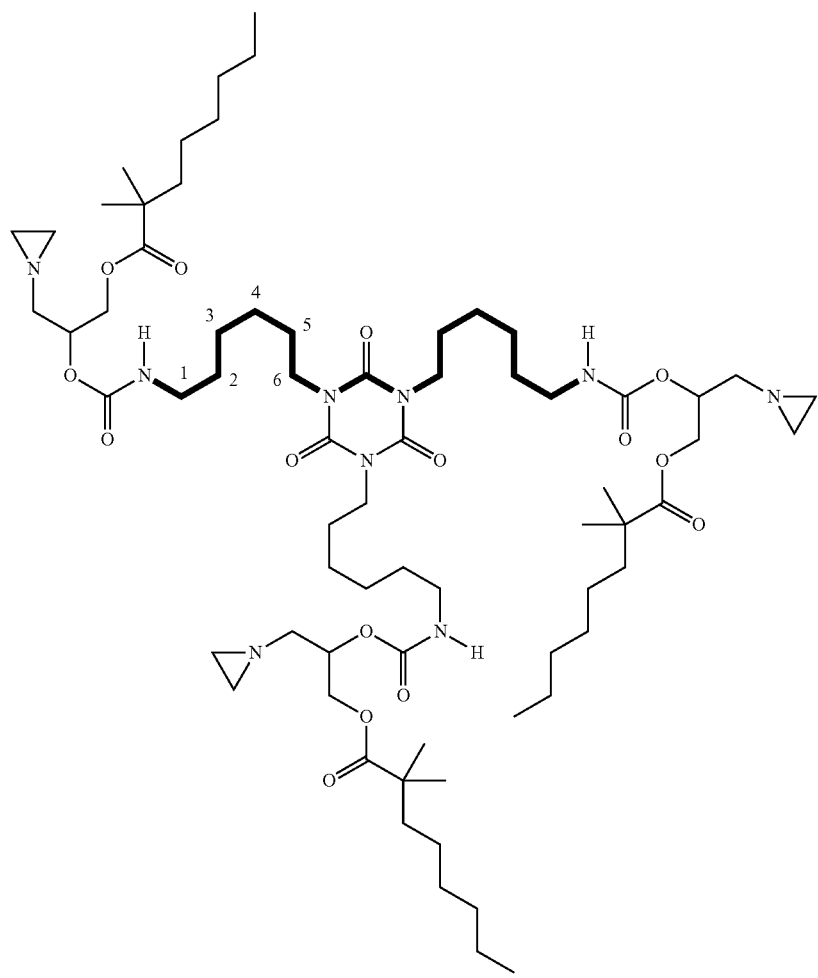

The multi-aziridine compound according to the invention preferably comprises one or more connecting groups, whereby each one of the connecting groups connects two of the structural units A and whereby each one of the connecting groups consists of at least one functionality selected from the group consisting of aliphatic hydrocarbon functionality (preferably containing from 1 to 8 carbon atoms), cycloaliphatic hydrocarbon functionality (preferably containing from 4 to 10 carbon atoms), aromatic hydrocarbon functionality (preferably containing from 6 to 12 carbon atoms), isocyanurate functionality, iminooxadiazindione functionality, ether functionality, ester functionality, amide functionality, carbonate functionality, urethane functionality, urea functionality, biuret functionality, allophanate functionality, uretdione functionality and any combination thereof. More preferably, the connecting groups are an array of consecutive functionalities whereby each functionality is selected from the group consisting of aliphatic hydrocarbon functionality (preferably containing from 1 to 8 carbon atoms), cycloaliphatic hydrocarbon functionality (preferably containing from 4 to 10 carbon atoms), aromatic hydrocarbon functionality (preferably containing from 6 to 12 carbon atoms), isocyanurate functionality, iminooxadiazindione functionality, ether functionality, ester functionality, amide functionality, carbonate functionality, urethane functionality, urea functionality, biuret functionality, allophanate functionality, uretdione functionality.

The following drawing shows in bold a connecting group for an example of a multi-aziridine compound according to the invention. In this example, the connecting group connecting two of the structural units A consists of the array of the following consecutive functionalities: aliphatic hydrocarbon functionality 1 (a linear $C_6H_{12}$), isocyanurate 2 (a cyclic $C_3N_3O_3$) functionality and aliphatic hydrocarbon functionality 3 (a linear $C_6H_{12}$).

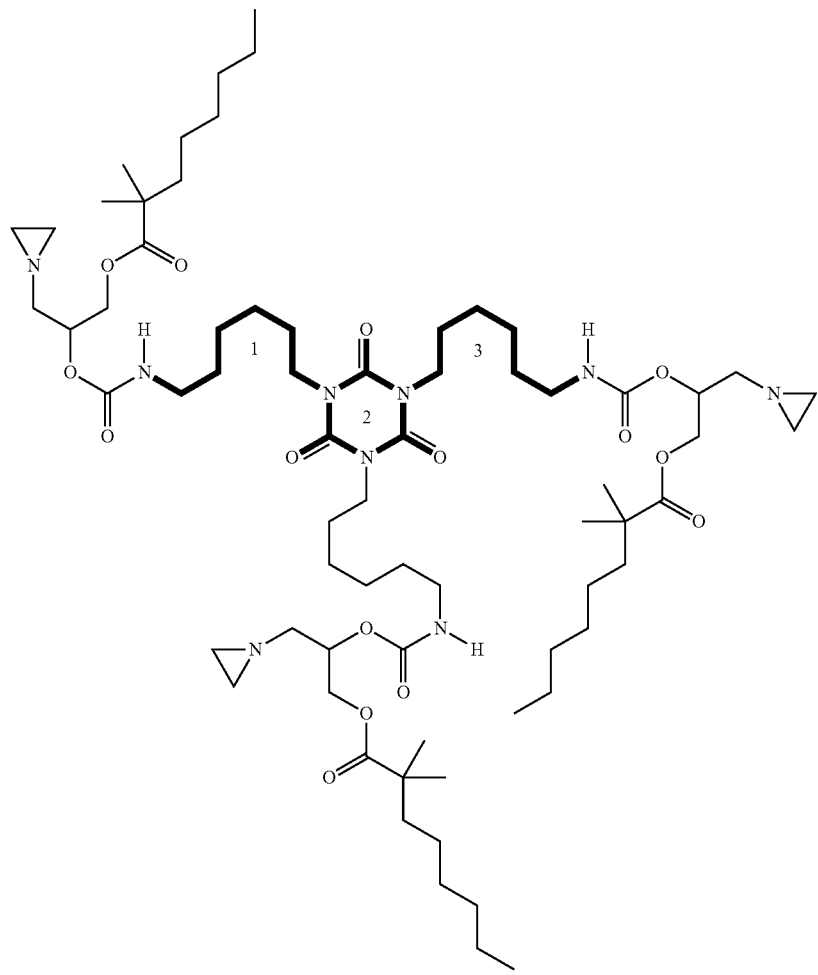

The following drawing shows in bold the connecting group for the following example of a multi-aziridine compound according to the invention. In this example, the connecting group connecting the two structural units A consists of the array of the following consecutive functionalities: aliphatic hydrocarbon functionality 1 (a linear $C_6H_{12}$), isocyanurate 2 (a cyclic $C_3N_3O_3$) and aliphatic hydrocarbon functionality 3 (a linear $C_6H_{12}$).

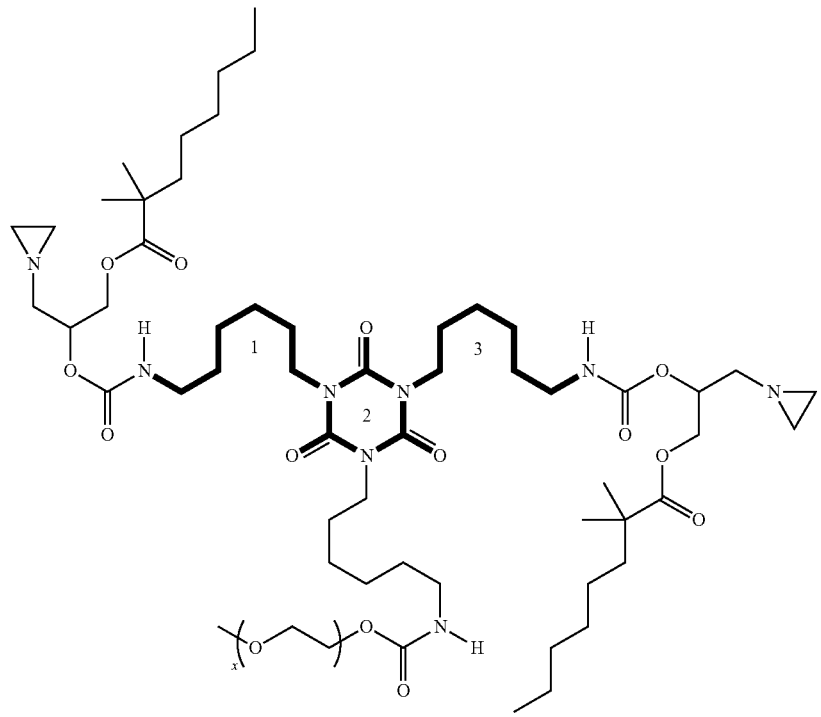

Any two of the structural units A present in the multi-aziridine compound of the invention are preferably connected via a connecting group which connecting group is as defined herein. Accordingly, each structural unit A present in the multi-aziridine compound of the invention is preferably connected to every other structural unit A with a connecting group which connecting group is as defined in the invention.

In case the multi-aziridine compound according to the invention has two structural units A, the multi-aziridine compound has one such connecting group connecting these two structural units. In case the multi-aziridine compound according to the invention has three structural units A, the multi-aziridine compound has three such connecting groups, whereby each one of the three connecting groups is connecting a structural unit A with another structural unit A.

The following drawing shows, for an example of a multi-aziridine compound having three structural units A, the three connecting groups whereby each one of the three connecting groups is connecting two structural units A. One connecting group consists of the array of the following consecutive functionalities: aliphatic hydrocarbon functionality 1 (a linear $C_6H_{12}$), isocyanurate 2 (a cyclic $C_3N_3O_3$) and aliphatic hydrocarbon functionality 3 (a linear $C_6H_{12}$) connecting the structural units A which are labelled as A1 and A2. For the connection between structural units A which are labelled as A1 and A3, the connecting group consists of the array of the following consecutive functionalities: aliphatic hydrocarbon functionality 1 (a linear $C_6H_{12}$), isocyanurate 2 (a cyclic $C_3N_3O_3$) and aliphatic hydrocarbon functionality 4 (a linear $C_6H_{12}$), while for the connection between the structural units A which are labelled as A2 and A3, the connecting group consists of the array of the following consecutive functionalities: aliphatic hydrocarbon functionality 3 (a linear $C_6H_{12}$), isocyanurate 2 (a cyclic $C_3N_3O_3$) and aliphatic hydrocarbon functionality 4 (a linear $C_6H_{12}$).

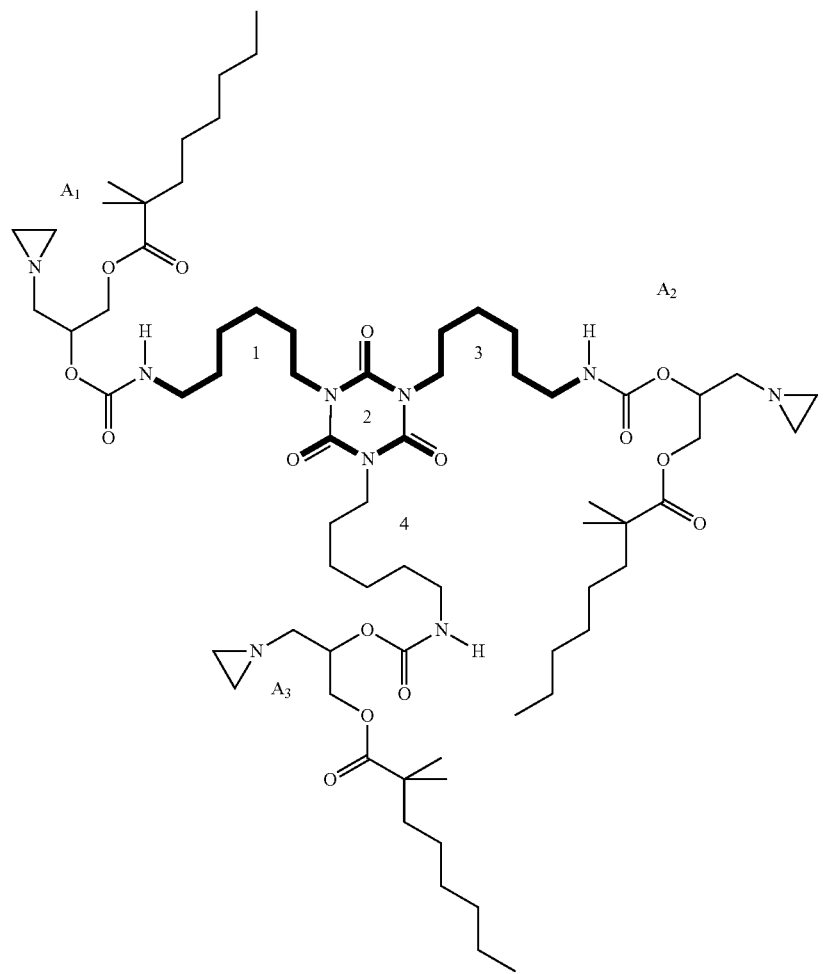

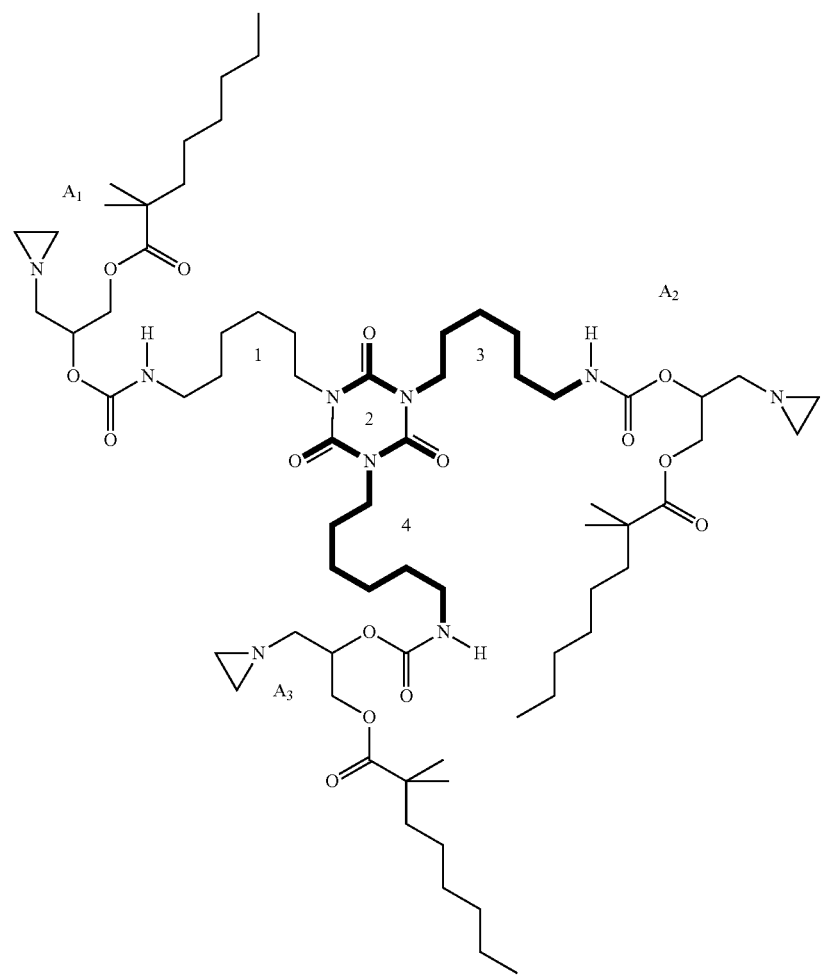

-continued

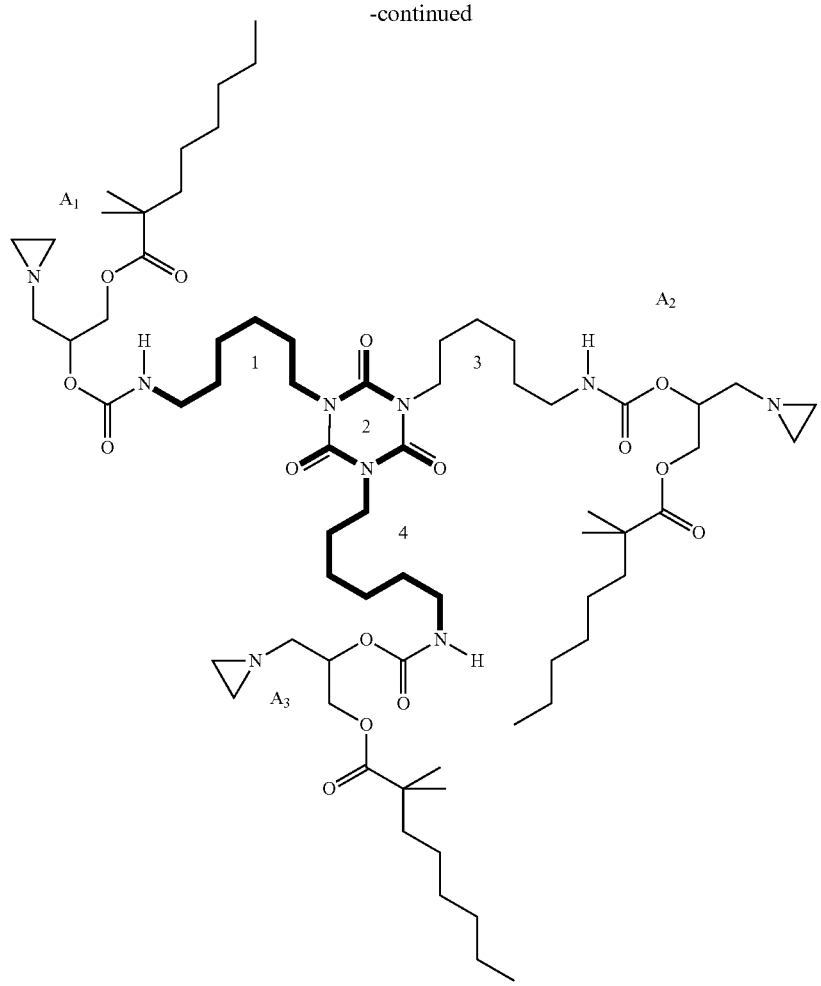

Preferably, the connecting groups consist of at least one functionality selected from the group consisting of aliphatic hydrocarbon functionality (preferably containing from 1 to 8 carbon atoms), cycloaliphatic hydrocarbon functionality (preferably containing from 4 to 10 carbon atoms), aromatic hydrocarbon functionality (preferably containing from 6 to 12 carbon atoms), isocyanurate functionality, iminooxadiazindione functionality, urethane functionality, urea functionality, biuret functionality and any combination thereof. The connecting groups preferably contain an isocyanurate functionality, an iminooxadiazindione functionality, a biuret functionality, allophanate functionality or an uretdione functionality. More preferably, the connecting groups contain an isocyanurate functionality or an iminooxadiazindione functionality. For the sake of clarity, the multi-aziridine compound may be obtained from the reaction product of one or more suitable compound B and a hybrid isocyanurate such as for example a HDI/IPDI isocyanurate, resulting in a multi-aziridine compound with a connecting group consisting of the array of the following consecutive functionalities: a linear $C_6H_{12}$ (i.e. an aliphatic hydrocarbon functionality with 6 carbon atoms), an isocyanurate functionality (a cyclic $C_3N_3O_3$) and

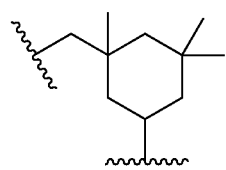 [SMILES: *CC1(C)CC(*)CC(C)(C)C1]

(i.e. a cycloaliphatic hydrocarbon functionality with 9 carbon atoms and an aliphatic hydrocarbon functionality with 1 carbon atom).

The term "aliphatic hydrocarbon functionality" refers to optionally branched alkyl, alkenyl and alkynyl groups. Whilst the optional branches of C atoms are part of the connecting group, they are not part of the linking chain. The term "cycloaliphatic hydrocarbon functionality" refers to cycloalkyl and cycloalkenyl groups optionally substituted with at least one aliphatic hydrocarbon group. Whilst the optional aliphatic hydrocarbon group substituents are part of the connecting group, they are not part of the linking chain. The optional aliphatic hydrocarbon group substituents are preferably alkyl groups. The term "aromatic hydrocarbon functionality" refers to a benzene ring optionally substituted with at least one aliphatic hydrocarbon group. The optional aliphatic hydrocarbon group substituents are preferably alkyl groups. Whilst the optional aliphatic hydrocarbon group substituents are part of the connecting group, they are not part of the linking chain.

On the connecting groups, one or more substituents may be present as pendant groups on the connection group, as shown in bold in for example the following multi-aziridine compound. These pendant groups are not part of the connecting groups.

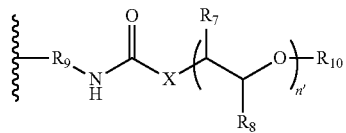

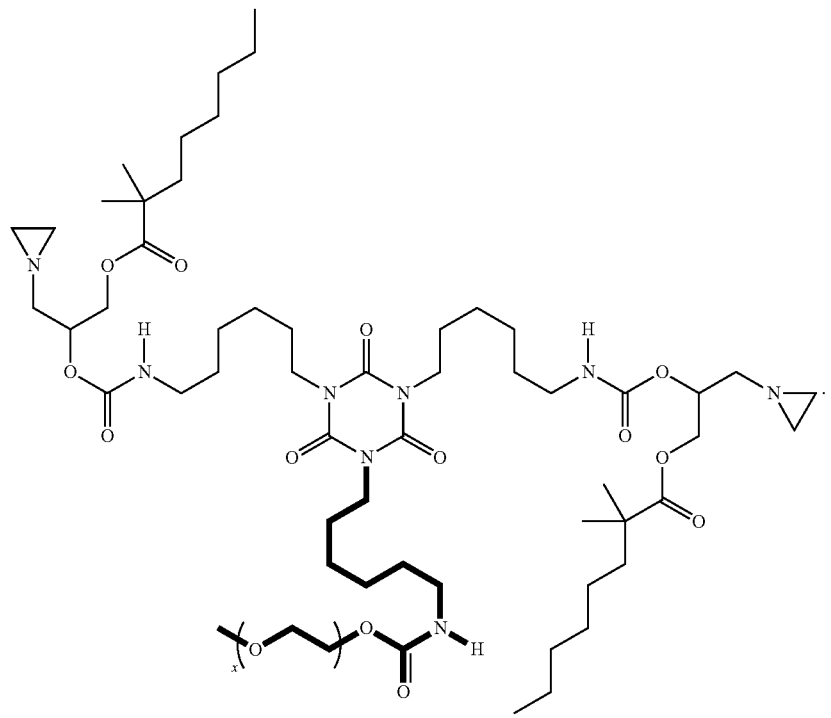

The pendant group preferably contains

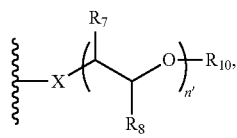

in which X, $R_7$, $R_3$, n' and $R_{10}$ are as described below. In an embodiment of the invention, the multi-aziridine compound comprises one or more connecting groups wherein each one of these connecting groups connects two of the structural units A, wherein the connecting groups consist of (i) at least two aliphatic hydrocarbon functionality or at least two cycloaliphatic hydrocarbon functionality and (ii) an isocyanurate functionality or an iminooxadiazindione functionality, and wherein a pendant group is present on a connecting group, whereby the pendant group has the following structural formula:

n' is the number of repeating units and is an integer from 1 to 50, preferably from 2 to 30, more preferably from 5 to 20.

X is O or NH, preferably X is O, $R_7$ and $R_3$ are independently H or $CH_3$ in each repeating unit, $R_9$ is an aliphatic hydrocarbon group, preferably containing from 1 to 8 carbon atoms, or a cycloaliphatic hydrocarbon group, preferably containing from 4 to 10 carbon atoms, and $R_{10}$ contains at most 20 carbon atoms and is an aliphatic, cycloaliphatic or aromatic hydrocarbon group or a combination thereof. In a preferred embodiment, one of $R_7$ and $R_3$ is H and the other $R_7$ or $R_3$ is $CH_3$. In another and more preferred embodiment, $R_7$ and $R_3$ are H. $R_{10}$ preferably is an aliphatic hydrocarbon group containing from 1 to 20 carbon atoms (preferably $CH_3$), a cycloaliphatic hydrocarbon group containing from 5 to 20 carbon atoms or an aromatic hydrocarbon group containing from 6 to 20 carbon atoms. The presence of the pendant group results in a decreased viscosity of the multi-aziridine compound and hence easier miscibility with the to be crosslinked polymer. In this embodiment, the multi-aziridine compound preferably contains 2 structural units A. In this embodiment the connecting group preferably consists of the array of the following consecutive functionalities: a first cycloaliphatic hydrocarbon functionality, an isocyanurate functionality or an iminooxadiazindione functionality, and a second cycloaliphatic hydrocarbon functionality, and $R_9$ is a cycloaliphatic hydrocarbon group, whereby the first and second cycloaliphatic hydrocarbon functionality and $R_9$ are identical, more preferably the connecting group consists of the array of the following consecutive functionalities: a first aliphatic hydrocarbon functionality, an isocyanurate functionality or an iminooxadiazindione functionality, and a second aliphatic hydrocarbon functionality, and $R_9$ is an aliphatic hydrocarbon group, whereby the first and second aliphatic hydrocarbon functionality and $R_9$ are identical.

In a preferred embodiment, the multi-aziridine compound according to the invention contains polyoxyethylene (—O—CH2-CH2-)$_x$ group(s) and/or polyoxypropylene (—O—CHCH3-CH2-)$_x$ group(s), preferably in an amount of at least 0.1 wt. %, more preferably at least 6 wt. %, more preferably at least 10 wt. % and preferably in an amount of less than 45 wt. %, more preferably less than 25 wt. % and most preferably less than 16 wt. %, relative to the multi-aziridine compound. Preferably, the multi-aziridine compound contains polyoxyethylene (—O—CH2-CH2-)$_x$ group(s), preferably in an amount of at least 0.1 wt. %, more preferably at least 6 wt. %, more preferably at least 10 wt. % and preferably in an amount of less than 45 wt. %, more preferably less than 25 wt. % and most preferably less than 16 wt. %, relative to the multi-aziridine compound. A multi-aziridine compound containing polyoxyethylene (—O—CH2-CH2-)$_x$ group(s) is preferably the reaction product of at least compound (B), a polyisocyanate and alkoxy poly(ethyleneglycol) (preferably methoxy poly(ethyleneglycol) (MPEG)) and/or poly(ethyleneglycol). The reaction product can be obtained by reacting at least compound B with the following structural formula:

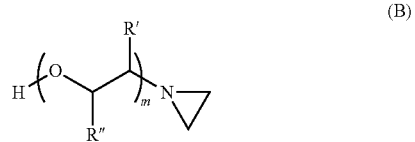

(B)

wherein R' and R" are as defined above, the polyisocyanate and alkoxy poly(ethyleneglycol) and/or poly(ethyleneglycol). The reaction product can also be obtained by reacting the polyisocyanate with alkoxy poly(ethyleneglycol) and/or poly(ethyleneglycol) and reacting the so-obtained compound with compound (B). The reaction product can also be obtained by reacting compound B with the polyisocyanate and reacting the so-obtained compound with alkoxy poly(ethyleneglycol) and/or poly(ethyleneglycol). The amount of alkoxy poly(ethyleneglycol) (preferably methoxy poly(ethyleneglycol) (MPEG)) and/or poly(ethyleneglycol) (PEG) chains with an average molecular weight higher than 2200 Daltons, preferably with an average molecular weight higher than 1600 Daltons in the multi-aziridine compound as defined above is preferably less than 35 wt. %, more preferably less than 15 wt. %, more preferably less than 5 wt. % and most preferably 0 wt. %. The methoxy poly(ethyleneglycol) (MPEG) and/or poly(ethyleneglycol) (PEG) chains present in the multi-aziridine compound preferably have an average molecular weight lower than 1100 Daltons, more preferably lower than 770 Daltons and most preferably lower than 570 Daltons. The average molecular weight is determined by multiplying the OH functionality of the polyol by the equivalent weight of the polyol. The OH functionality of the polyol is given by the supplier of the polyol. In case the polyol is a diol, the OH functionality is 2. The equivalent weight of the polyol is calculated by dividing 56100 by the OH number of the polyol. The OH number of the polyol is measured by titration a known mass of polyol according to ISO 14900 (2017) and is expressed as mg KOH/g polyol.

An isocyanurate functionality is defined as

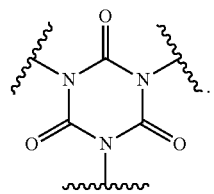 [SMILES: *n1c(=O)n(*)c(=O)n(*)c1=O]

An iminooxadiazindione functionality is defined as

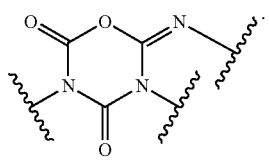 [SMILES: */N=c1/oc(=O)n(*)c(=O)n1*]

An allophanate functionality is defined as

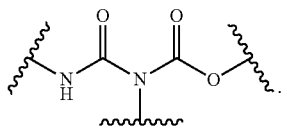 [SMILES: *NC(=O)N(*)C(=O)O*]

An uretdione functionality is defined a

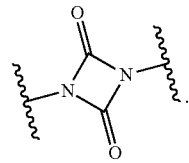 [SMILES: *N1C(=O)N(*)C1=O]

A biuret functionality is defined as

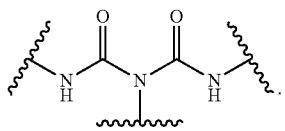 [SMILES: *NC(=O)N(*)C(=O)N*]

In a preferred embodiment of the invention, the connecting groups present in the multi-aziridine compound of the invention consist of the following functionalities: (i) at least one aliphatic hydrocarbon functionality and/or at least one cycloaliphatic hydrocarbon functionality and (ii) an isocyanurate functionality or iminooxadiazindione functionality or allophanate functionality or uretdione functionality and (iii) optionally at least one aromatic hydrocarbon functionality. Preferably, the connecting groups present in the multi-aziridine compound of the invention consist of the following functionalities: (i) at least one aliphatic hydrocarbon functionality and/or at least one cycloaliphatic hydrocarbon functionality and (ii) an isocyanurate functionality or iminooxadiazindione functionality and (iii) optionally at least one aromatic hydrocarbon functionality. A very suitable way of obtaining such multi-aziridine compound is reacting compound B with the following structural formula:

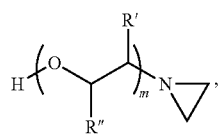

with a polyisocyanate with aliphatic reactivity. The term "a polyisocyanate with aliphatic reactivity" being intended to mean compounds in which all of the isocyanate groups are directly bonded to aliphatic or cycloaliphatic hydrocarbon groups, irrespective of whether aromatic hydrocarbon groups are also present. The polyisocyanate with aliphatic reactivity can be a mixture of polyisocyanates with aliphatic reactivity. Compounds based on polyisocyanate with aliphatic reactivity have a reduced tendency of yellowing over time when compared to a similar compound but based on polyisocyanate with aromatic reactivity. The term "a polyisocyanate with aromatic reactivity" being intended to mean compounds in which all of the isocyanate groups are directly bonded to a benzene or a naphthalene group, irrespective of whether aliphatic or cycloaliphatic groups are also present. Preferred polyisocyanates with aliphatic reactivity are 1,5-pentamethylene diisocyanate PDI, 1,6-hexamethylene diisocyanate HDI, isophorone diisocyanate IPDI, 4,4'-dicyclohexyl methane diisocyanate H12MDI, 2,2,4-trimethyl hexamethylene diisocyanate, 2,4,4-trimethyl hexamethylene diisocyanate, tetramethylxylene diisocyanate TMXDI (all isomers) and higher molecular weight variants like for example their isocyanurates, or iminooxadiazindiones. More preferred polyisocyanates with aliphatic reactivity are isocyanurates or iminooxadiazindiones of 1,5-pentamethylene diisocyanate PDI, of 1,6-hexamethylene diisocyanate HDI, of isophorone diisocyanate IPDI, of 4,4'-dicyclohexyl methane diisocyanate H12MDI, of 2,2,4-trimethyl hexamethylene diisocyanate, of 2,4,4-trimethyl hexamethylene diisocyanate, of tetramethylxylene diisocyanate TMXDI. In this embodiment, preferably the connecting groups consist of the array of the following consecutive functionalities: aliphatic hydrocarbon functionality, aromatic hydrocarbon functionality and aliphatic hydrocarbon functionality (for example when using TMXDI for preparing the multi-aziridine compound) or the connecting groups consist of the array of the following consecutive functionalities: cycloaliphatic hydrocarbon functionality, aliphatic hydrocarbon functionality and cycloaliphatic hydrocarbon functionality (for example when using H12MDI for preparing the multi-aziridine compound) or more preferably, the connecting groups consist of the array of the following consecutive functionalities: aliphatic hydrocarbon functionality, isocyanurate functionality or iminooxadiazindione functionality, and aliphatic hydrocarbon functionality. Most preferably, in this embodiment, the connecting group consists of the array of the following consecutive functionalities: aliphatic hydrocarbon functionality, isocyanurate functionality, and aliphatic hydrocarbon functionality (for example when using an isocyanurate of 1,6-hexamethylene diisocyanate and/or an isocyanurate of 1,5-pentamethylene diisocyanate for preparing the multi-aziridine compound).

The multi-aziridine compound according to the invention preferably contains at least 5 wt. %, more preferably at least 5.5. wt. %, more preferably at least 6 wt. %, more preferably at least 9 wt. %, more preferably at least 12 wt. % and preferably less than 25 wt. %, preferably less than 20 wt. % of urethane bonds. The multi-aziridine compound according to the invention preferably has an aziridine equivalent weight (molecular weight of the multi-aziridine compound divided by number of aziridinyl groups present in the multi-aziridine compound) of at least 250, more preferably at least 280 and even more preferably at least 320 Daltons and preferably at most 2500, more preferably at most 1000 and even more preferably at most 500 Daltons.

The multi-aziridine compound can be stabilized if desired with amines, preferably 0.1 to 5 wt. % more preferred 0.1 to 2.5 wt % and most preferred 0.1 to 1 wt % of a secondary or tertiary amine. Preferred amines include ammonia, dimethyl ethanol amine, diisopropylamine, isopropanol amine, diethyl ethanol amine, N,N dimethyl isopropanol amine, 3-dimethylamino-1-propanol, 2-[2-(dimethylamino)ethoxy}ethanol, N-ethyl morpholine, dimethyl benzyl amine and triethyl amine. Alternatively, alkali hydroxides can be used like for example NaOH, LiOH, KOH as well as combinations of amines with alkali hydroxides.

The multi-aziridine compound according to the invention is preferably obtained by reacting at least a polyisocyanate and a compound B with the following structural formula:

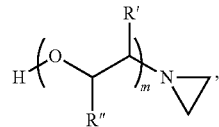

Wherein R', R" and m and its preferments are as defined above and whereby the molar ratio of compound B to polyisocyanate is from 2 to 6, more preferably from 2.1 to 5 and most preferably from 2.4 to 3. Most preferred m=1. Reacting the polyisocyanate with compound B may be carried out by bringing equivalent amounts of the polyisocyanate into contact with the compound B at a temperature in the range of from 0 to 110° C., more suitable from 20° C. to 110° C., more suitable from 40° C. to 95° C., even more suitable from 60 to 85° C. in the presence of for example a tin catalyst such as for example dibutyltin dilaurate or a bismuth catalyst such as for example bismuth neodecanoate. A solvent may be used, such as for example dimethylformamide DMF, acetone and/or methyl ethyl ketone. The polyisocyanate contains at least 2 isocyanate groups, preferably at least 2.5 isocyanate groups on average and more preferably at least 2.8 isocyanate groups on average. Mixtures of polyisocyanates may also be used as starting materials. Preferred polyisocyanates are polyisocyanates with aliphatic reactivity. The term "a polyisocyanate with aliphatic reactivity" being intended to mean compounds in which all of the isocyanate groups are directly bonded to aliphatic or cycloaliphatic hydrocarbon groups, irrespective of whether aromatic hydrocarbon groups are also present. The polyisocyanate with aliphatic reactivity can be a mixture of polyisocyanates with aliphatic reactivity. Preferred polyisocyanates with aliphatic reactivity are 1,5-pentamethylene diisocyanate PDI, 1,6-hexamethylene diisocyanate HDI, isophorone diisocyanate IPDI, 4,4'-dicyclohexyl methane diisocyanate H12MDI, 2,2,4-trimethyl hexamethylene diisocyanate, 2,4,4-trimethyl hexamethylene diisocyanate, p-tetra-methylxylene diisocyanate (p-TMXDI) and its meta isomer, and higher molecular weight variants like for example their isocyanurates or iminooxadiazindiones or allophanates or uretdiones. More preferred polyisocyanates with aliphatic reactivity are isocyanurates or iminooxadiazindiones of 1,5-pentamethylene diisocyanate PDI, of 1,6-hexamethylene diisocyanate HDI, of isophorone diisocyanate IPDI, of 4,4'-dicyclohexyl methane diisocyanate H12MDI, of 2,2,4-trimethyl hexamethylene diisocyanate, of 2,4,4-trimethyl hexamethylene diisocyanate, of tetramethylxylene diisocyanate TMXDI. Even more preferred polyisocyanates with aliphatic reactivity are an isocyanurate or iminooxadiazindione of 1,6-hexamethylene diisocyanate, an isocyanurate or iminooxadiazindione of 1,5-pentamethylene diisocyanate, an isocyanurate or iminooxadiazindione of IPDI. A suitable HDI containing iminooxadiazindione trimer is Desmodur® N3900, obtainable from Covestro. A suitable HDI containing allophonate is Desmodur® XP2860, obtainable from Covestro. A suitable HDI containing uretdione is Desmodur® N3400, obtainable from Covestro. Suitable HDI based isocyanurates trimers can for example be obtained from Covestro (Desmodur® N3600), Vencorex (Tolonate™ HDT LV), Asahi Kasei (Duranate™ TPA-100), Evonik (Vestanat® HT 2500/LV) and Tosoh (Coronate® HXR LV). Methods for preparing compound (B) and derivatives are known in the art. For example, synthesis of 1-(aziridin-1-yl)propan-2-ol is described by A. Baklien, M. V. Leeding, J. Kolm Aust. J. Chem. 1968, 21, 1557-1570.

Compound B is preferably obtained by reacting at least a non-OH functional monoepoxide compound with ethyleneimine. The non-OH functional monoepoxide may be a mixture of different non-OH functional monoepoxides. Non-limited examples of non-OH functional monoepoxide are propylene oxide, 2-ethyl oxirane, n-butylglycidylether, 2-ethylhexylglycidylether, phenyl glycidyl ether, 4-tert-butylphenyl 2,3-epoxypropyl ether (=t-butyl phenyl glycidyl ether), cresol glycidyl ether (ortho or para) and glycidyl neodecanoate. The non-OH functional monoepoxide is preferably selected from the group consisting of propylene oxide (CAS number 75-56-9), 2-ethyl oxirane (CAS number 106-88-7), n-butylglycidylether (CAS number 2426-08-6), 2-ethylhexylglycidylether (CAS number 2461-15-6), glycidyl neodecanoate (CAS number 26761-45-5) and any mixture thereof. More preferably, the non-OH functional monoepoxide is selected from the group consisting of propylene oxide (CAS number 75-56-9), 2-ethyl oxirane (CAS number 106-88-7), n-butylglycidylether (CAS number 2426-08-6), 2-ethylhexylglycidylether (CAS number 2461-15-6), glycidyl neodecanoate (CAS number 26761-45-5) and any mixture thereof. Most preferably, the non-OH functional monoepoxide compound is selected from the group consisting of n-butylglycidylether, 2-ethylhexylglycidylether, glycidyl neodecanoate and any mixture thereof.

The multi-aziridine compound according to the invention is preferably obtained in a process comprising at least the following steps (i) and (ii):

(i) Reacting ethyleneimine with at least a non-OH functional monoepoxide compound to obtain compound B, and (ii) Reacting compound B with a polyisocyanate.

Step (i) can be carried out, for example, by bringing one equivalent of the epoxide compound into contact with one equivalent of the aziridine at a temperature in the range of from −10° C. to 60° C., more suitable from −5° C. to 50° C., even more suitable from 0 to 40° C. at atmospheric pressure. The reaction (step (ii)) of the adduct (compound (B)) obtained in step (i) with the polyisocyanate can be carried out, for example, by bringing equivalent amounts of the polyisocyanate into contact with the adduct at a temperature in the range of from 20° C. to 110° C. more suitable from 40° C. to 95° C. at atmospheric pressure, in the presence of for example a tin catalyst such as for example dibutyltin dilaurate.

Examples of preferred multi-aziridine compounds according to the invention are

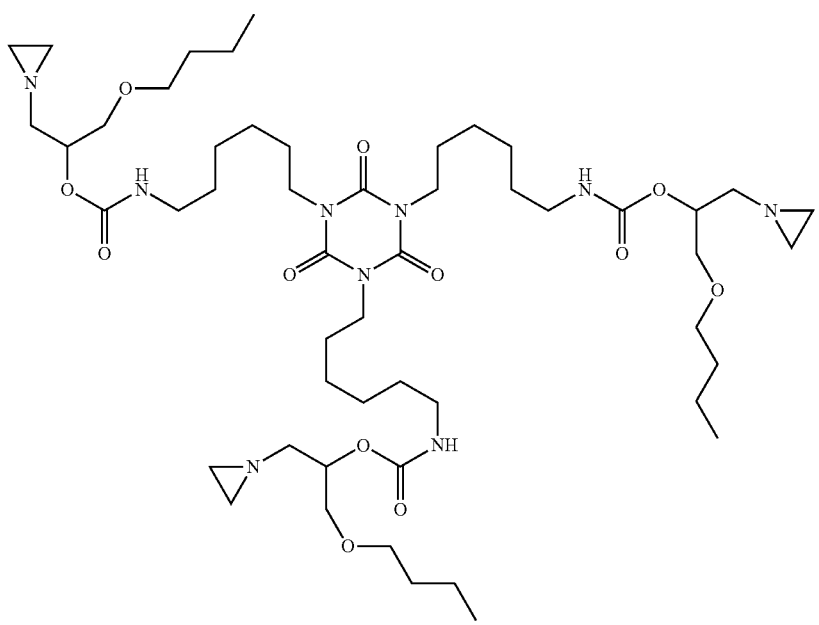

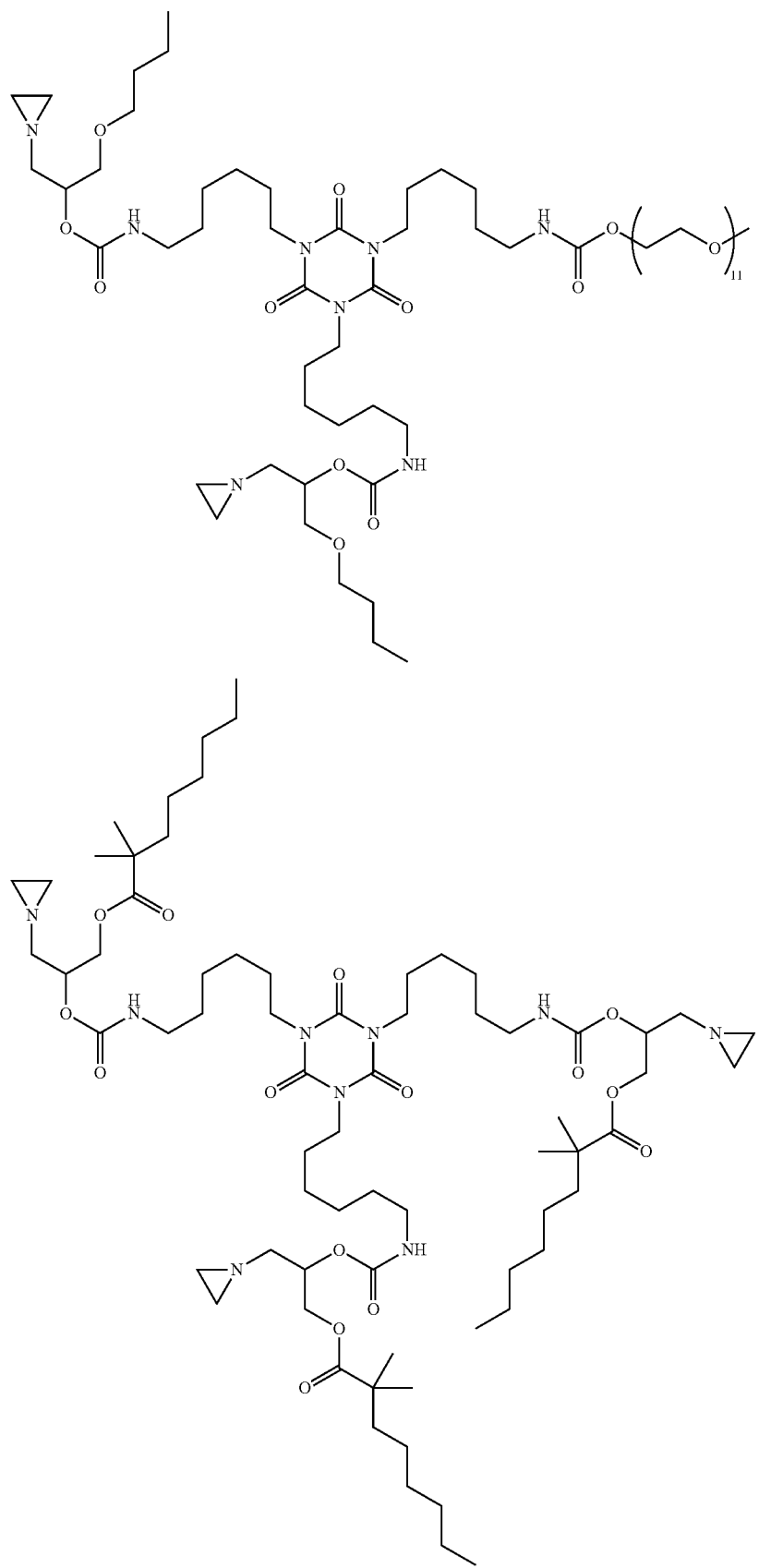

A further aspect of the current invention is a crosslinker composition comprising at least one multi-aziridine compound as defined above and further comprising at least one additional component, such as for example remaining starting materials, side-products and/or solvent used for preparing the multi-aziridine compound according to the invention. The crosslinker composition may contain only one multi-aziridine compound according to the invention but may also contain more than one multi-aziridine compound according to the invention. Mixtures of multi-aziridine compounds are for example obtained when a mixture of polyisocyanates as starting material to prepare the multi-aziridine are used. After having obtained the multi-aziridine compound(s) according to the invention, the multi-aziridine compound(s) according to the invention may be separated, the reaction product may be used without further purification or solvent used for preparing the multi-aziridine compound(s) may be removed from the composition obtained in the preparation of the multi-aziridine compound(s) of the invention. The amount of multi-aziridine compounds according to the invention in the crosslinker composition is usually at least 10 wt. %, usually often at least 15 wt. % and most often at least 25 wt. % relative to total amount of the composition. The amount of multi-aziridine compounds according to the invention in the crosslinker composition is preferably at least 60 wt. %, more preferably at least 80 wt. % and most preferably at least 99 wt. %, relative to total amount of the crosslinker composition. The molecular weight of the multi-aziridine compounds in the crosslinker composition is in the range of from 840 Daltons to 5000 Daltons. Preferred molecular weights are as described above and molecular weights of the multi-aziridine compounds are determined using MALDI-TOF-MS as described in the experimental part herein below. MALDI-TOF-MS means matrix-assisted laser desorption ionization time of flight mass spectroscopy.

The amount of aziridine functional molecules, present in the crosslinker composition according to the invention, having a molecular weight lower than 250 Daltons, more preferably lower than 350 Daltons, even more preferably lower than 450 Daltons, even more preferably lower than 550 Daltons and even more preferably lower than 820 Daltons is preferably lower than 1.5 wt. %, more preferably lower than 1 wt. %, more preferably lower than 0.5 wt. % and most preferably lower than 0.1 wt. %, relative to the total weight of the crosslinker composition, whereby the molecular weight is determined using LC-MS as described in the experimental part below.

The average number of aziridinyl groups with structural formula (C)

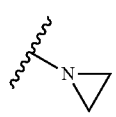
(C)

per aziridinyl-containing molecule in the crosslinker composition is preferably at least 1.8, more preferably at least 2, more preferably at least 2.2 and preferably less than 10, more preferably less than 6 and most preferably less than 4. Most preferably, the average number of aziridinyl groups per aziridinyl-containing molecule in the composition is from 2.2 to 3. The calculated average amount of urethane bonds is at least 5 wt. %, more preferably at least 5.5. wt. %, more preferably at least 6 wt. %, more preferably at least 9 wt. %, more preferably at least 12 wt. % and preferably and less than 25 wt. %, preferably less than 20 wt. % of urethane bonds, relative to the total weight of the multi-aziridine compounds according to the invention present in the crosslinker composition.

In view of the potential water sensitivity of the multi-aziridine compounds according to the invention, the crosslinker composition is preferably free of substantial amount of water and more preferably is free of water. Free of substantial amount of water means less than 15 wt. %, preferably less than 5 wt. %, more preferably less than 1 wt. % and most preferably less than 0.1 wt. %. In view of the potential water sensitivity of the multi-aziridine compounds according to the invention, water is preferably not deliberately (i.e. small amounts of water may be present in the compounds used to prepare the multi-aziridine compound(s) according to the invention) be added to the composition.

The multi-aziridine compounds according to the invention preferably have a Brookfield viscosity of at least 10000 mPa·s at 25° C., more preferably at least 20000, more preferably at least 50000 and preferably at most 1000000, more preferably at most 500000, and even more preferably at most 200000 mPa·s at 25° C. As used herein, the Brookfield viscosity is determined according to ISO 2555-89. In an alternative embodiment the viscosity of the multi-aziridine was measured with a Brookfield with spindle S63, @ 25° C. at 80% solids in dimethyl formamide (DMF). The viscosity as measured according to this method is preferably in the range of 300 to 20000 mPas, more preferably in the range of from 500 to 12000 and most preferably in the range of from 700 to 3000 mPas.

The multi-aziridine compounds according to the invention or the crosslinker composition comprising at least one multi-aziridine compound as defined above can be advantageously used as crosslinking agent for crosslinking a carboxylic acid functional polymer dissolved and/or dispersed, preferably dispersed, in an aqueous medium.

A further aspect of the present invention is a two-component coating system comprising a first component and a second component which is separate and distinct from each other, wherein the first component comprising a carboxylic acid functional polymer dissolved and/or dispersed, preferably dispersed, in an aqueous medium and wherein the second component comprising a multi-aziridine compound as defined above or wherein the second component is a crosslinker composition as defined above, whereby the first and second component are separately stored, since the crosslinking reaction between the crosslinking agent and the polymer to be crosslinked may start immediately after mixing the crosslinking agent with the aqueous composition of polymer to be crosslinked. Just prior to application of the coating composition, the first and second component of the two-component system are mixed to obtain a coating composition comprising aziridinyl groups Q and carboxylic acid groups. The pH of the first component is, prior to combining with the second component, preferably at least 7, more preferably at least 7.5, even more preferably at least 8 and even more preferably at least 8.5.

The carboxylic acid functional polymer present in the first component of the two-component coating system contains carboxylic acid groups and/or carboxylate groups which are preferably free of a covalent bond that blocks these groups to chemically react with the aziridine moiety present in the multi-aziridine compound. As used herein, the amount of carboxylic acid groups present in the carboxylic acid functional polymer is the summed amount of deprotonated and protonated carboxylic acid groups present in the polymer to be crosslinked, i.e. in the carboxylic acid functional polymer. Thus, the amount of carboxylic acid groups present in the carboxylic acid functional polymer is the summed amount of carboxylate groups and carboxylic acid groups present in the carboxylic acid functional polymer. The polymer to be crosslinked preferably comprises carboxylate groups which are at least partially neutralized with base. Preferably at least part of the base is a volatile base. Preferably, at least a part of the carboxylic acid groups present in the carboxylic acid functional polymer to be crosslinked are subjected to deprotonation to obtain carboxylate groups. The deprotonation is effected by neutralizing the carboxylic acid functional polymer with a base. Examples of suitable bases are ammonia, secondary amines, tertiary amines, LiOH, NaOH and/or KOH. Examples of secondary amines and tertiary amines are described above. Preferred bases are tertiary amines. Preferred tertiary amines are as described above. Most preferred is triethylamine.

Non-limited examples of crosslinkable carboxylic acid functional polymers are vinyl polymers like styrene-acrylics, (meth)acrylic copolymers, vinyl acetate (co)polymers such as for example vinyl acetate vinyl chloride ethylene polymers, polyurethanes, polycondensates like polyesters, polyamides, polycarbonates and hybrids of any of these polymers where at least one of the two polymers have a carboxylic acid functionality. The carboxylic acid functional polymer is preferably selected from the group consisting of polyesters, polycarbonates, polyamides, vinyl polymers, polyacrylates, polymethacrylates, poly(acrylate-co-methacrylate)s, polyurethanes, poly(urethane-co-acrylate)s, poly(urethane-co-methacrylate)s, poly(urethane-co-acrylate-co-methacrylate), polyureas, and mixtures thereof. Preferably by vinyl polymer is meant a polymer comprising reacted residues of styrene and acrylates and/or methacrylates. In an embodiment of the invention, preferred crosslinkable carboxylic acid functional polymers are selected from the group consisting of vinyl polymers, polyacrylates, polymethacrylates, poly(acrylate-co-methacrylate)s and mixtures thereof. In another embodiment, the carboxylic acid functional polymer is selected from the group consisting of polyurethanes, poly(urethane-co-acrylate)s, poly(urethane-co-methacrylate)s, poly(urethane-co-acrylate-co-methacrylate), polyureas, and mixtures thereof. The present invention further also relates to a coating composition obtained by mixing the first and second component of the two-component coating system just prior to application of the coating composition, whereby the coating composition comprises aziridinyl groups Q and carboxylic acid groups in an amount such that the stoichiometric amount (SA) of aziridinyl groups Q on carboxylic acid groups is preferably from 0.1 to 2.0, more preferably from 0.2 to 1.5, even more preferably from 0.25 to 0.95, most preferably from 0.3 to 0.8. The pH of the coating composition is preferably at least 7.5, more preferably at least 8, more preferably at least 8.5 and even more preferably at least 9.

The present invention further relates to a substrate having a coating obtained by (i) applying a coating composition as described above to a substrate and (ii) drying the coating composition by evaporation of volatiles. The drying of the coating composition is preferably affected at a temperature lower than 160° C., preferably at a temperature lower than 90° C., more preferably at a temperature lower than 50° C. and most preferably at ambient temperature. The coating composition according to the invention can be applied to any kind of substrate, such as for example wood, leather, concrete, textile, plastic, vinyl floors, glass, metal, ceramics, paper, wood plastic composite, glass fiber reinforced materials. The thickness of the dry coating on the substrate is preferably from 1 to 200 micron, more preferably from 5 to 150 micron and most preferably from 15 to 90 microns. In case the coating composition is an ink composition, the thickness of the dry ink is preferably from 0.005 to 35 micron, more preferably from 0.05 to 25 micron and most preferably from 4 to 15 microns.

The present invention is now illustrated by reference to the following examples. Unless otherwise specified, all parts, percentages and ratios are on a weight basis.

AV Determination

The acid value on solid material (AV) of a sample is determined based on the ASTM D1639-90(1996)e1 standard. In the procedure, the sample, dissolved in a good solvent, is titrated with alcoholic potassium hydroxide solution of a known concentration (KOH). The difference in titration volume between the sample and a blank is the measure of the acid value on solids, according to the following formula: $AV=[(Vblank-Vsample)*N_{KOH}*56.1]/(W*S/100)$, where AV is acid number on solids in mg KOH/g solid material, Vblank is the volume of KOH solution used in the blank, Vsample is the volume of KOH solution used in the sample, $N_{KOH}$ is the normality of the KOH solution, W is the sample weight in grams and S is the solids content of the sample in %. Measurements are performed in duplicate using a potentiometric endpoint on a Metrohm 702SM Titrino titrator (accepting the measurement if the difference between duplicates is <0.1 mg KOH/g solid material).

Chemical Resistance

Chemical resistance testing based on DIN 68861-1:2011-01 standard.

Unless indicated otherwise the chemical resistance is tested as follows: Coating compositions are composed at 0.9 stoichiometric amounts (SA) of total carboxylic acid-reactive functional groups (e.g. aziridine) compared to carboxylic acid functional groups. Coating compositions are treated as described in the examples, and then cast at 100 μm wet layer thickness using a wire bar applicator. After casting, films were dried for 1 hour at 25° C., then annealed at 50° C. for 16 hours. Subsequently, a piece of cotton wool was soaked in 1:1 Ethanol:demineralized water (by weight) and placed on the film for 60 minutes (unless indicated otherwise). After removal of the cotton wool and overnight recovery, the spots were scored according to the following ranks:

1 Complete coating degradation
2 Structural damage to the coating
3 Severe marking on coating, visible from multiple directions
4 Slight marking on coating, visible from specific angles
5 No observed marking or gloss change Viscosity Measurements:

The apparent viscosity is determined according to ISO 2555:2018. The measurement is performed at 23° C. on a Brookfield DVE-LV viscometer (single-cylinder geometry) at 60 rpm. The spindle is selected from S62, S63 or S64, using the lowest numbered spindle (i.e. the largest spindle) that yields a reading between 10% and 100% torque.

Low Molecular Weight Fraction by LC-MS

LC system: Agilent 1290 Infinity II; Detector #1: Agilent 1290 Infinity II PDA; Detector #2: Agilent iFunnel 6550 Q-TOF-MS.

LC-MS analysis for the low molecular weight fraction was performed using the following procedure. A solution of ~100 mg/kg of material was prepared gravimetrically in methanol and stirred. 0.5 µl of this solution was injected into a UPLC equipped with ESI-TOF-MS detection. The column used was a 100×2.1 mm, 1.8 um, Waters HSS T3 C18 operated at 40° C. Flow rate was 0.5 ml·min$^{-1}$. Solvents used were 10 mM NH$_4$CH$_3$COO in water set to pH 9.0 with NH$_3$ (Eluent A), Acetonitrile (B) and THF (C). Two binary gradients were applied from 80/20 A/B to 1/99 A/B in 10 minutes and from 1/99 A/B to 1/49/50 A/B/C in 5 minutes, after which starting conditions are applied (80/20 A/B). Assuming linear MS response of all components over all response ranges and an equal ionization efficiency for all components, Total Ion Current signals were integrated. In case of coelution extracted ion chromatograms of that particular species were integrated. Dividing the integrated signal of a particular low-molecular weight peak by the total integrated sample signal yields the fraction of that low molecular weight species.

MALDI-ToF-MS

All MALDI-ToF-MS spectra were acquired using a Bruker Ultraflextreme MALDI-ToF mass spectrometer. The instrument is equipped with a Nd:YAG laser emitting at 1064 nm and a collision cell (not used for these samples). Spectra were acquired in the positive-ion mode using the reflectron, using the highest resolution mode providing accurate masses (range 60-7000 m/z). Cesium Tri-iodide (range 0.3-3.5 kDa) was used for mass calibration (calibration method: IAV Molecular Characterisation, code MC-MS-05). The laser energy was 20%. The samples were dissolved in THF at approx. 50 mg/mL. The matrix used was: DCTB (trans-2-[3-(4-tert-Butylphenyl)-2-methyl-2-propenylidene]malononitrile), CAS Number 300364-84-5. The matrix solution was prepared by dissolving 20 mg in 1 mL of THF.

Sodium iodide was used as salt (NaI, CAS Number 7681-82-5); 10 mg was dissolved in 1 ml THF with a drop of MeOH added. Ratio sample:matrix:salt=10:200:10 (µl), after mixing, 0.5 µL was spot on MALDI plate and allowed to air-dry. The peaks measured in the MALDI spectrum are sodium adducts of multi-aziridine compounds, and in the context of this specification the molecular weight (MW) of the multi-aziridine compound corresponds to MW=Obs. [M+M$_{cation}$]−M$_{cation}$, where Obs. [M+M$_{cation}$] is the MALDI-TOF MS peak and M$_{cation}$ is the exact mass of the cation used for making the adduct (in this case sodium with M$_{cation}$=23.0 Da). Multi-aziridine compounds can be identified by comparing the MW with the exact molecular mass (i.e. the sum of the—non-isotopically averaged—atomic masses of its constituent atoms) of a theoretical structure, using a maximum deviation of 0.6 Da.

Synthesis of P1, a Waterborne Polyurethane

A one-liter flask (equipped with a thermometer and an overhead stirrer), was charged with 29.9 grams of dimethylol propionic acid, 282.1 grams of a polypropylene glycol with a calculated average molecular weight (M) of 2000 Da and an OH-value of 56±2 mg KOH/g polypropylene glycol), 166.5 grams of a polypropylene glycol with a calculated average molecular weight (M) of 1000 Da and an OH-value of 112±2 mg KOH/g polypropylene glycol, and 262.8 grams of isophorone diisocyanate (the average molecular weight of each of the polyols is calculated from its OH-value according to the equation: M=2*56100/[OH-value in mg KOH/g polypropylene glycol). The reaction mixture was placed under N$_2$ atmosphere, heated to 50° C. and subsequently 0.07 g dibutyltin dilaurate were added to the reaction mixture. An exothermic reaction was observed; however proper care was taken in order for the reaction temperature not to exceed 97° C. The reaction was maintained at 95° C. for an hour. The NCO content of the resultant polyurethane P1' was 7.00% on solids as determined according to the ISO 14896 Method A (year 2009) (theoretically 7.44%) and the acid value of the polyurethane P1' was 16.1±1 mg KOH/g polyurethane P1'. The polyurethane P1' was cooled down to 60° C. and 18.7 grams of triethylamine were added, and the resulting mixture was stirred for 30 minutes. Subsequently, an aqueous dispersion of the polyurethane P1' (the aqueous dispersion of the polyurethane P1' is further referred to as P1) was prepared as follows: the thus prepared mixture of the polyurethane P1' and triethylamine was fed—at room temperature over a time period of 60 minutes—to a mixture of 1100 grams of demineralized water, 19.5 grams of nonylphenol ethoxylate (9 ethoxylate groups), and 4.0 grams of triethylamine. After the feed was completed, the mixture was stirred for additional 5 minutes, and subsequently 111.2 grams of hydrazine (16 wt % solution in water) were added to the mixture. The aqueous dispersion of the polyurethane P1' thus prepared was stirred for an additional 1 h and P1 was obtained.

Genotoxicity Testing

Genotoxicity of examples and comparatives was evaluated by the ToxTracker® assay (Toxys, Leiden, the Netherlands). The ToxTracker assay is a panel of several validated Green Fluorescent Protein (GFP)-based mouse embryonic stem (mES) reporter cell lines that can be used to identify the biological reactivity and potential carcinogenic properties of newly developed compounds in a single test. This methodology uses a two step-approach.

In the first step a dose range finding was performed using wild-type mES cells (strain B4418). 20 different concentrations for each compound was tested, starting at 10 mM in DMSO as highest concentration and nineteen consecutive 2-fold dilutions.

Next, genotoxicity of examples and comparatives was evaluated using specific genes linked to reporter genes for the detection of DNA damage; i.e. Bscl2 (as elucidated by U.S. Pat. No. 9,695,481B2 and EP2616484B1) and Rtkn (Hendriks et. al. Toxicol. Sci. 2015, 150, 190-203) biomarkers. Genotoxicity was evaluated at 10, 25 and 50% cytotoxicity in absence and presence of rat S9 liver extract-based metabolizing systems (aroclor1254-induced rats, Moltox, Boone, NC, USA). The independent cell lines were seeded in 96-well cell culture plates, 24 h after seeding the cells in the 96-well plates, fresh ES cell medium containing the diluted test substance was added to the cells. For each tested compound, five concentrations are tested in 2-fold dilutions. The highest sample concentration will induce significant cytotoxicity (50-70%). In case of no or low cytotoxicity, 10 mM or the maximum soluble mixture concentration is used as maximum test concentration. Cytotoxicity is determined by cell count after 24 h exposure using a Guava easyCyte 10HT flow cytometer (Millipore).

GFP reporter induction is always compared to a vehicle control treatment. DMSO concentration is similar in all wells for a particular compound and never exceeds 1%.

All compounds were tested in at least three completely independent repeat experiments. Positive reference treatment with cisplatin (DNA damage) were included in all experiments. Metabolic was evaluated by addition of S9 liver extract. Cells are exposed to five concentrations of the test compound in the presence of S9 and required co-factors (RegenSysA+B, Moltox, Boone, NC, USA) for 3 h. After washing, cells are incubated for 24 h in fresh ES cell medium. Induction of the GFP reporters is determined after 24 h exposure using a Guava easyCyte 10HT flow cytometer (Millipore). Only GFP expression in intact single cells is determined. Mean GFP fluorescence and cell concentrations in each well is measured, which is used for cytotoxicity assessment. Data was analyzed using ToxPlot software (Toxys, Leiden, the Netherlands). The induction levels reported are at compound concentrations that induce 10%, 25% and 50% cytotoxicity after 3 h exposure in the presence of S9 rat liver extract and 24 h recovery or alternatively after 24 h exposure when not in the presence of S9 rat liver extract.

A positive induction level of the biomarkers is defined as equal to or higher than a 2-fold induction at at least one of 10, 25 and 50% cytotoxicity in the absence or presence of the metabolizing system rat S9 liver extract; a weakly positive induction as higher than 1.5-fold and lower than 2-fold induction at at least one of 10, 25 and 50% cytotoxicity (but lower than 2-fold at 10, 25 and 50% cytotoxicity) in the absence or presence of the metabolizing system rat S9 liver extract and a negative as lower than or equal to a 1.5-fold induction at 10, 25 and 50% cytotoxicity in the absence and presence of rat S9 liver extract-based metabolizing systems.

Components and Abbreviations Used:

Dimethylformamide (CAS No. 68-12-2) was obtained from Acros Organics (a division of Thermo Fisher Scientific).

Di(propylene glycol) dimethyl ether (Proglyde DMM, CAS No. 111109-77-4) was obtained from Dow Inc Trimethylolpropane tris(2-methyl-1-aziridinepropionate), CAS No. 64265-57-2, CX-100 was obtained from DSM.

Pentaerythritol tris(3-(1-aziridinyl)propionate), CAS number 57116-45-7 was obtained from ABCR.

Potassium carbonate (CAS No. 584-08-7) was obtained from Alfa Aesar (a division of Thermo Fisher Scientific).

IPDI (5-Isocyanato-1-(isocyanatomethyl)-1,3,3-trimethylcyclohexane, Desmodur® I, isophorone diisocyanate, CAS No. 4098-71-9) was obtained from Covestro.

Polyethylene Glycol Monomethyl Ether (CAS No. 9004-74-4) with a number average molecular weight of 1000 Da was obtained from Tokyo Chemical Industry Co., Ltd.

n-butylglycidyl ether (CAS No. 2426-08-6) was obtained from Alfa Aesar (a division of Thermo Fisher Scientific).

Desmodur® N3600 and Desmodur® N3900 were obtained from Covestro. 1-methoxy-2-propanol acetate (propylene glycol methyl ether acetate, CAS No. 108-65-6) was obtained from Shell Chemicals.

1-(2-hydroxyethyl)ethyleneimine) (CAS No. 1072-52-2) was obtained from Tokyo Chemical Industry Co., Ltd.

Jeffamine® XTJ-436 (CAS No. 118270-87-4) was obtained from Huntsman Bismuth neodecanoate (CAS No. 34364-26-6) obtained from TIB chemicals AG (Mannheim, Germany).

Ethylene imine (CAS No. 151-56-4) was obtained from Menadiona S. L. (Palafolls, Spain)

Cardura E10P (CAS No. 26761-45-5) was obtained from Hexion Inc.

H12MDI (4,4'-Methylenebis(phenyl isocyanate, Desmodur® W, CAS No. 101-66-8) from Covestro.

Hydrazine (16% solution in water, CAS No. 302-01-2) was obtained from Honeywell.

Dimethylol propionic acid (DMPA, CAS No. 4767-03-7) was obtained from Perstop Polyols.

Triethylamine (TEA, CAS No. 121-44-8) was obtained from Arkema 1-propanol (CAS No. 71-23-8) was obtained from Sigma-Aldrich.

Tin 2-ethylhexanoate (CAS No. 301-10-0) was obtained from Sigma-Aldrich.

Dibutyltindilaurate (CAS No. 77-58-7) was obtained from Sigma-Aldrich.

Tegomer® D3403 was obtained from Evonik.

Polypropyleneglycol with a number average molecular weight of 1000 Da and with a number average molecular weight of 2000 Da was obtained from BASF. 3-Methyl-1-phenyl-2-phospholene-1-oxide (CAS No. 707-61-9) was obtained from Sigma-Aldrich.

Sodium lauryl sulphate (30% solution in water, CAS No. 73296-89-6) was obtained from BASF.

Methyl methacrylate (CAS No. 80-62-6) was obtained from Lucite Int. n-Butyl acrylate (CAS No. 141-32-2) was obtained from Dow Chemical.

Methacrylic acid (CAS No. 79-41-4) was obtained from Lucite Int.

Ammonium persulphate (CAS No. 7727-54-0) was obtained from United Initiators.

Ammonia (25% solution in water, CAS No. 1336-21-6) was obtained from Merck. 1-Butanol (CAS No. 71-36-3) was obtained from Sigma-Aldrich.

COMPARATIVE EXAMPLE 1

Comparative Example 1 is CX-100, trimethylolpropane tris(2-methyl-1-aziridinepropionate), obtained from DSM. Chemical structure is shown below.

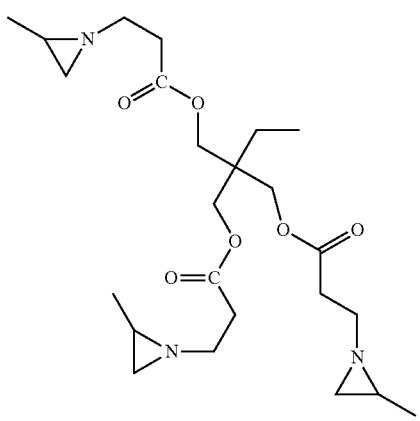

For reference, the performance of trimethylolpropane tris(2-methyl-1-aziridinepropionate) as a crosslinker was assessed using spot tests on coating surfaces, based on procedures from the DIN 68861-1:2011-01 standard. For these tests, 0.23 parts of the compound were mixed with 0.60 parts of Proglyde™ DMM (dipropylene glycol dimethyl ether, mixture of isomers) and incubated at 80° C. for 10 minutes under regular agitation. Subsequently, 0.56 parts of the resulting solution were added to 20 parts of P1 under continuous stirring, and the resulting mixture was further stirred for 30 minutes. Afterwards, this coating composition was filtered and applied to Leneta test cards using 100 μm wire rod applicators (Test C1-1). The films were dried for 16 hours at 25° C., then annealed at 50° C. for 1 hour and further dried for 24 hours at 25° C. Subsequently, a piece of cotton wool was soaked in 1:1 EtOH demineralized water and placed on the film for various timespans. After removal of the EtOH and 60 minutes recovery, the following results were obtained (a score of 1 indicates complete degradation of the film, 10 indicates no damage visible):

Ethanol Spot Test

| Sample | 30 min | 60 min | 120 min | 300 min |
|---|---|---|---|---|
| Test C1-1 | 8 | 7 | 7 | 6 |

Genotoxicity Test

| | Without S9 rat liver extract | | | | | | With S9 rat liver extract | | | | | |
|---|---|---|---|---|---|---|---|---|---|---|---|---|
| | Bscl 2 | | | Rtkn | | | Bscl 2 | | | Rtkn | | |
| concentration | | | | | | | | | | | | |
| → | 10 | 25 | 50 | 10 | 25 | 50 | 10 | 25 | 50 | 10 | 25 | 50 |
| Comp. Ex. 1 | 1.2 | 1.5 | 2.0 | 1.4 | 2.0 | 3.2 | 1.7 | 2.3 | 2.1 | 3.0 | 4.3 | 3.4 |

The genotoxicity test results show that the crosslinker of Comparative Example 1 is genotoxic.

COMPARATIVE EXAMPLE 2

15.0 grams of Desmodur N 3600 and 75 grams of dimethylformamide were charged to a reaction flask equipped with a thermometer. The mixture was stirred with a mechanical upper stirrer under a nitrogen atmosphere. The mixture was than heated to 50° C., whereafter 6.80 grams of 1-(2-hydroxyethyl)ethyleneimine was added. 15 minutes later 0.03 grams of bismuth neodecanoate was charged to the reaction flask, which was then heated further to 60° C. Samples were taken at regular intervals and the reaction progress was monitored using a Bruker Alpha FT-IR spectrometer until no NCO-stretch at 2200-2300 cm$^{-1}$ was observed. The solvent was removed in vacuo to obtain a clear, slightly yellowish highly viscous liquid. The calculated molecular weight of the theoretical main component was 765.47 Da, chemical structure is shown below.

Molecular weight was confirmed by Maldi-TOF-MS: Calcd. [M+K+]=804.43 Da; Obs. [M+K+]=804.27 Da.

Genotoxicity Test

| | Without S9 rat liver extract | | | | | | With S9 rat liver extract | | | | | |
|---|---|---|---|---|---|---|---|---|---|---|---|---|
| | Bscl 2 | | | Rtkn | | | Bscl 2 | | | Rtkn | | |
| concentration | | | | | | | | | | | | |
| → | 10 | 25 | 50 | 10 | 25 | 50 | 10 | 25 | 50 | 10 | 25 | 50 |
| Comp. Ex. 2 | 1.1 | 1.3 | 1.4 | 1.7 | 2.4 | 2.8 | 1.4 | 1.9 | 1.9 | 2.0 | 3.4 | 3.0 |

The genotoxicity test results show that the crosslinker of Comparative Example 2 is genotoxic.

COMPARATIVE EXAMPLE 3

2.60 grams of 1-(aziridin-1-yl)propan-2-ol, 0.02 grams of bismuth neodecanoate and 32 grams of dimethylformamide were charged to a reaction flask equipped with a thermometer. The mixture was stirred with a mechanical upper stirrer under a nitrogen atmosphere and heated to 50° C. A solution of 5.00 grams of Desmodur N 3600 in 32 grams of dimethylformamide was then added dropwise in 15 minutes to the reaction flask, where after the mixture was heated further to 70° C. Samples were taken at regular intervals and the reaction progress was monitored using a Bruker Alpha FT-IR spectrometer until no NCO-stretch at 2200-2300 cm$^{-1}$ was observed. The solvent was removed in vacuo to obtain an opaque highly viscous liquid. The calculated molecular weight of the theoretical main component was 807.52 Da, chemical structure is shown below.

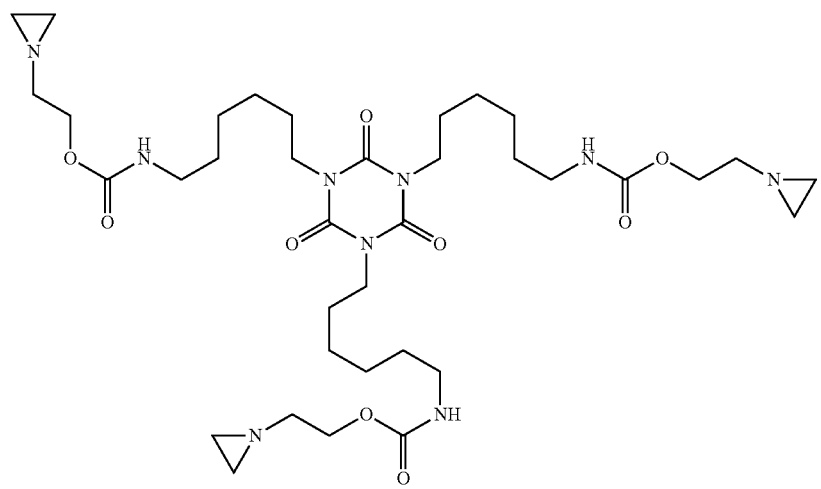 [SMILES: O=C(NCCCCCCn1c(=O)n(CCCCCCNC(=O)OCCN2CC2)c(=O)n(CCCCCCNC(=O)OCCN2CC2)c1=O)OCCN1CC1]

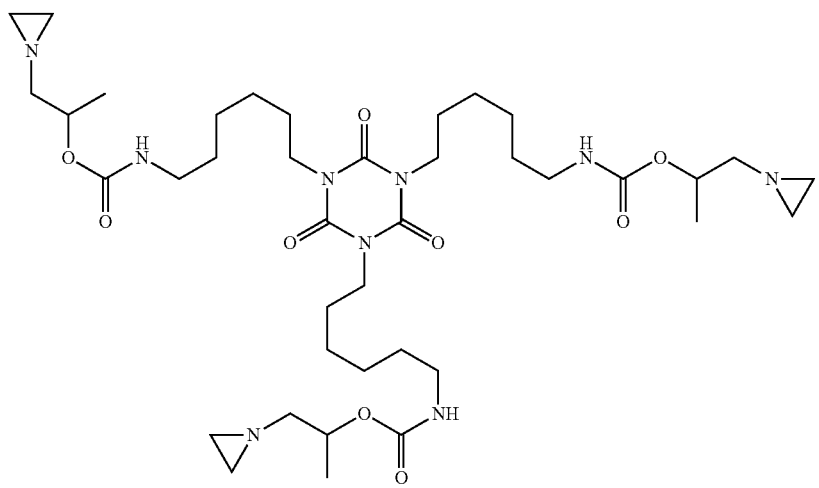 [SMILES: CC(CN1CC1)OC(=O)NCCCCCCn1c(=O)n(CCCCCCNC(=O)OC(C)CN2CC2)c(=O)n(CCCCCCNC(=O)OC(C)CN2CC2)c1=O]

Molecular weight was confirmed by Maldi-TOF-MS: Calcd. [M+Na+]=830.52 Da; Obs. [M+Na+]=830.47 Da.
Genotoxicity Test

|  | Without S9 rat liver extract | | | | | | With S9 rat liver extract | | | | | |
|---|---|---|---|---|---|---|---|---|---|---|---|---|
| concentration | Bscl 2 | | | Rtkn | | | Bscl 2 | | | Rtkn | | |
| → | 10 | 25 | 50 | 10 | 25 | 50 | 10 | 25 | 50 | 10 | 25 | 50 |
| Comp. Ex. 3 | 1.1 | 1.3 | 1.3 | 1.3 | 1.8 | 1.9 | 1.3 | 1.8 | 1.8 | 1.3 | 2.1 | 2.2 |

The genotoxicity test results show that the crosslinker of Comparative Example 3 is genotoxic.

EXAMPLE 1

A round bottom flask equipped with a condenser was placed under a $N_2$ atmosphere and charged with ethylene imine (50.0 gram), n-butyl glycidyl ether (108.0 gram) and $K_2CO_3$ (5.00 gram) and heated to 40° C. in 30 min, after which the mixture was stirred for 48 h at T=40° C. After filtration the excess of EI was removed in vacuo, followed by further purification via vacuum distillation, resulting in a colorless low viscous liquid. 3.45 grams of the resulting material (1-(aziridin-1-yl)-3-butoxypropan-2-ol) was charged to a reaction flask equipped with a thermometer, together with 0.02 grams of bismuth neodecanoate and 15 grams of dimethylformamide. The mixture was stirred with a mechanical upper stirrer under a nitrogen atmosphere and heated to 50° C. A solution of 4.00 grams of Desmodur® N 3600 in 8 grams of dimethylformamide was then added dropwise in 45 minutes to the reaction flask, while keeping the reaction temperature constant at 50° C. Samples were taken at regular intervals and the reaction progress was monitored using a Bruker Alpha FT-IR spectrometer until no change in NCO-stretch at 2200-2300 $cm^{-1}$ was observed. Subsequently, 0.13 grams of 1-butanol were added to the mixture, followed by further reaction to complete disappearance of aforementioned NCO-stretch peak. Concentration of the solution in vacuo to a 25 wt % solution yielded a slightly viscous liquid.

The calculated theoretical molecular weight of the main component was 1023.69 Da, chemical structure is shown below.

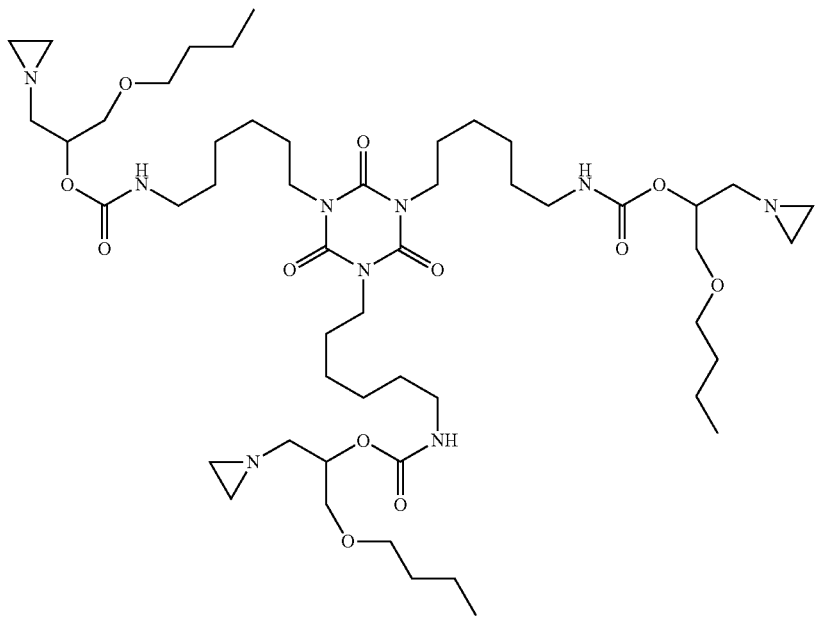 [SMILES: CCCCOCC(CN1CC1)OC(=O)NCCCCCCn1c(=O)n(CCCCCCNC(=O)OC(COCCCC)CN2CC2)c(=O)n(CCCCCCNC(=O)OC(COCCCC)CN2CC2)c1=O]

Molecular weight was confirmed by Maldi-TOF-MS: Calcd. [M+Na+]=1046.69 Da; Obs. [M+Na+]=1046.72 Da.

The following components with a mass below 840 Da were determined by LC-MS and quantified:

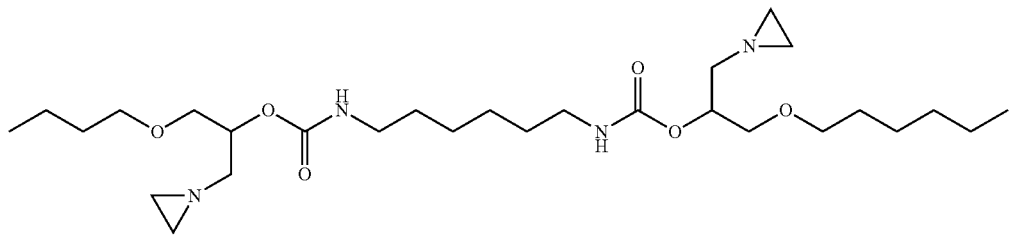 [SMILES: CCCCCCOCC(CN1CC1)OC(=O)NCCCCCCNC(=O)OC(COCCCC)CN1CC1]

was present in the composition at 0.48 wt. % and

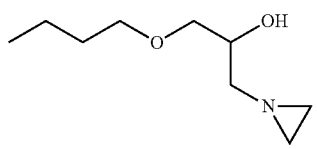

was present at less than 0.01 wt. %.

Performance of the synthesized compound as a crosslinker was assessed using spot tests on coating surfaces, based on procedures from DIN 68861-1:2011-01 standard. For these tests, 1.4 parts of the crosslinker solution were added to 10 parts of P1 under continuous stirring, and the resulting mixture was further stirred for 30 minutes. Afterwards, this coating composition was filtered and applied to Leneta test cards using 100 μm wire rod applicators (Test 1-1). For reference, films were also cast from the same composition lacking a crosslinker (Test 1-2). The films were dried for 16 hours at 25° C., then annealed at 50° C. for 1 hour and further dried for 24 hours at 25° C. Subsequently, a piece of cotton wool was soaked in 1:1 EtOH: demineralized water and placed on the film for various timespans. After removal of the EtOH and 60 minutes recovery, the following results were obtained (a score of 1 indicates complete degradation of the film, 5 indicates no damage visible):

Ethanol Spot Test

| Sample | 60 min | 240 min |
|---|---|---|
| Test 1-1 | 5 | 4 |
| Test 1-2 | 1 | 1 |

Genotoxicity Test

| | Without S9 rat liver extract | | | | | | With S9 rat liver extract | | | | | |
|---|---|---|---|---|---|---|---|---|---|---|---|---|
| | Bscl 2 | | | Rtkn | | | Bscl 2 | | | Rtkn | | |
| concentration → | 10 | 25 | 50 | 10 | 25 | 50 | 10 | 25 | 50 | 10 | 25 | 50 |
| Ex. 1 | 1.1 | 1.1 | 1.0 | 1.0 | 1.0 | 0.9 | 1.1 | 1.1 | 1.2 | 1.0 | 1.1 | 1.1 |

The genotoxicity test results show that the crosslinker composition of Example 1 is non-genotoxic.

COMPARATIVE EXAMPLE 4

1.00 grams of 4,4'-methylenebis(cyclohexyl isocyanate) and 4.8 grams of dimethylformamide were charged to a

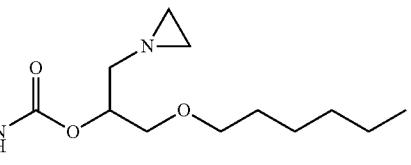

reaction flask equipped with a thermometer. The mixture was stirred with a mechanical upper stirrer under a nitrogen atmosphere and heated to 50° C. 0.02 grams of bismuth neodecanoate was added to the solution. A solution of 1.21 grams 1-(aziridin-1-yl)-3-butoxypropan-2-ol in 2.28 grams of dimethylformamide was then added dropwise in 15 minutes to the reaction flask, where after the mixture was heated further to 80° C. Samples were taken at regular intervals and the reaction progress was monitored using a Bruker Alpha FT-IR spectrometer until no change in NCO-stretch at 2200-2300 cm$^{-1}$ was observed. Subsequently, 0.05 grams of 1-butanol were added to the mixture, followed by further reaction to complete disappearance of aforementioned NCO-stretch peak. Evaporation of the solvent in vacuo yielded a highly viscous opaque liquid. The calculated theoretical molecular weight of the main component was 608.45 Da, chemical structure is shown below.

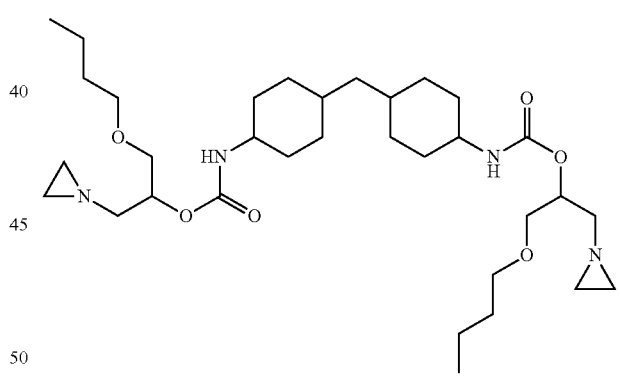

Molecular weight was confirmed by Maldi-TOF-MS: Calcd. [M+Na+]=631.45 Da; Obs. [M+Na+]=631.45 Da.

Genotoxicity Test

| | Without S9 rat liver extract | | | | | | With S9 rat liver extract | | | | | |
|---|---|---|---|---|---|---|---|---|---|---|---|---|
| | Bscl 2 | | | Rtkn | | | Bscl 2 | | | Rtkn | | |
| concentration → | 10 | 25 | 50 | 10 | 25 | 50 | 10 | 25 | 50 | 10 | 25 | 50 |
| Comp. Ex 4 | 1.1 | 1.4 | 1.6 | 1.2 | 1.5 | 2.1 | 1.2 | 1.5 | 1.4 | 1.1 | 1.6 | 1.9 |

The genotoxicity test results show that the crosslinker composition of Comp Ex 4 is genotoxic.

EXAMPLE 2

A round bottom flask equipped with a condensor was placed under a $N_2$ atmosphere and charged with ethylene imine (50.0 gram), n-butyl glycidyl ether (108.0 gram) and $K_2CO_3$ (5.00 gram) and heated to 40° C. in 30 min, after which the mixture was stirred for 48 h at T=40° C. After filtration the excess of EI was removed in vacuo, followed by further purification via vacuum distillation, resulting in a colorless low viscous liquid.

0.67 grams of the resulting material (1-(aziridin-1-yl)-3-butoxypropan-2-ol) was charged to a feeding funnel together with 0.54 grams of a poly(ethylene glycol) monomethyl ether with an average Mn of 500 Da and 2.28 grams of dimethylformamide. This mixture was fed in 15 minutes to a reaction flask equipped with a thermometer and filled with 1.00 grams of Desmodur® N 3600, 4.54 grams of DMF and 0.02 grams of bismuth neodecanoate at 50° C., while the mixture was stirred with a mechanical upper stirrer under a nitrogen atmosphere. After the feed was completed, the mixture was heated further to 80° C. Samples were taken at regular intervals and the reaction progress was monitored using a Bruker Alpha FT-IR spectrometer until no change in NCO-stretch at 2200-2300 cm$^{-1}$ was observed. Subsequently, 0.03 grams of 1-butanol were added to the mixture, followed by further reaction to complete disappearance of aforementioned NCO-stretch peak. Concentration of the solution in vacuo to a 25 wt % solution yielded a slightly viscous liquid.

The calculated molecular weights of the theoretical main components were 1023.69 Da (three aziridines), 1322.84 Da (two aziridines, 10 EG repeating units) and 1366.87 Da (two aziridines, 11 EG repeating units).

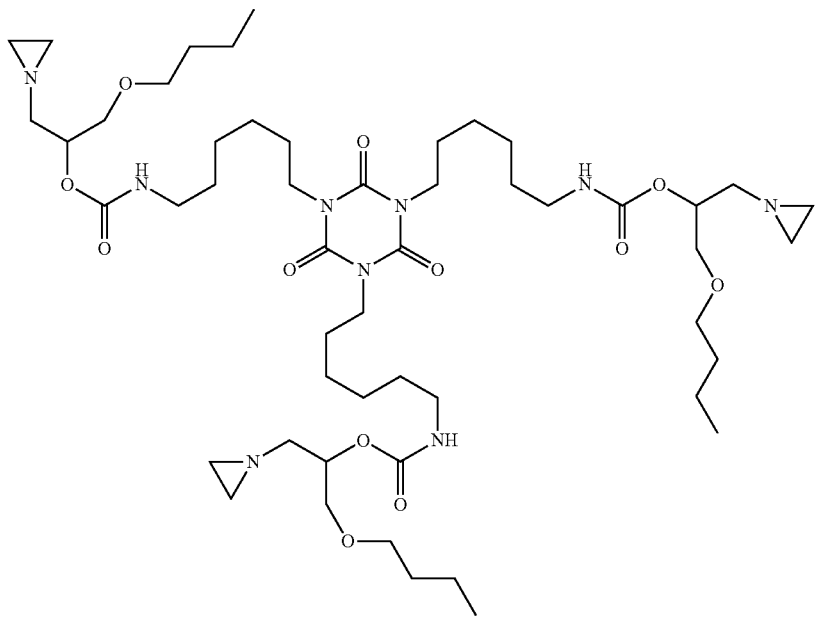

Molecular weight was confirmed by Maldi-TOF-MS:
Calcd. [M+Na+]=1046.69 Da; Obs. [M+Na+]=1046.16 Da.
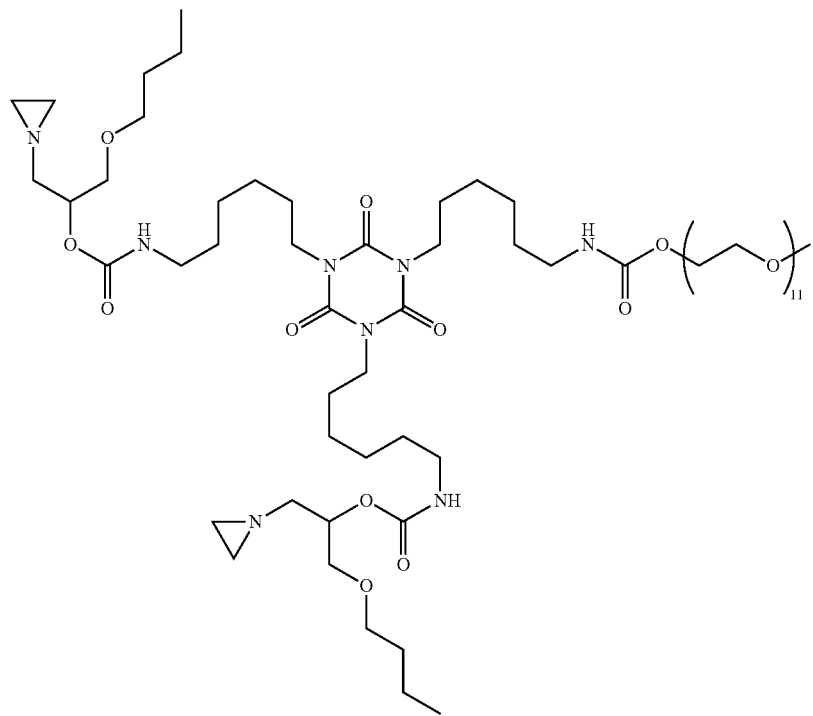
Molecular weight was confirmed by Maldi-TOF-MS:
Calcd. [M+Na+]=1345.84 Da; Obs. [M+Na+]=1345.31 Da.
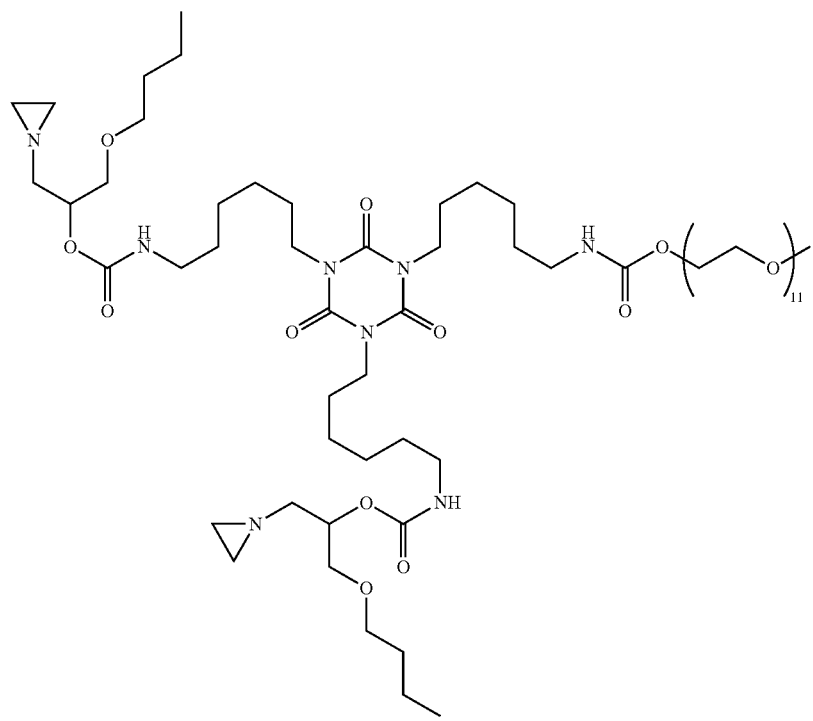
Molecular weight was confirmed by Maldi-TOF-MS:
Calcd. [M+Na+]=1389.87 Da; Obs. [M+Na+]=1389.52 Da.

The following components with a mass below 820 Da were determined by LC-MS and quantified:

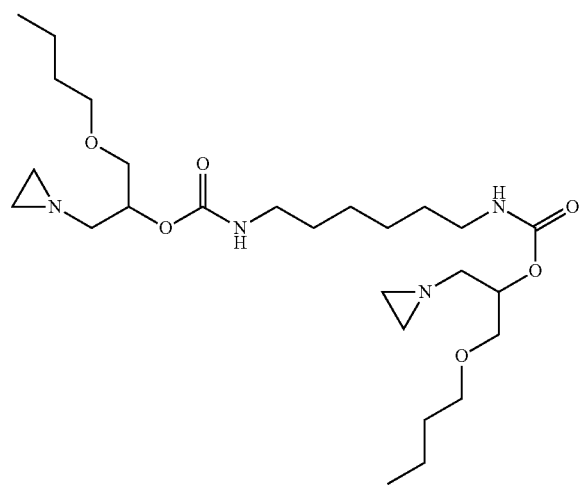 [SMILES: CCCCOCC(CN1CC1)OC(=O)NCCCCCCNC(=O)OC(COCCCC)CN1CC1]

was present in the composition at less than 0.01 wt % and

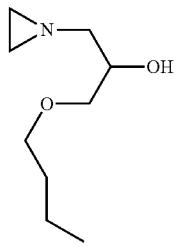

was present at less than 0.01 wt. %.

Performance of the synthesized compound as a crosslinker was assessed using spot tests on coating surfaces, based on procedures from the DIN 68861-1:2011-01 standard. For these tests, 2.4 parts of the crosslinker solution were added to 10 parts of P1 under continuous stirring, and the resulting mixture was further stirred for 30 minutes. Afterwards, this coating composition was filtered and applied to Leneta test cards using 100 μm wire rod applicators (Test 2-1). For reference, films were also cast from the same composition lacking a crosslinker (Test 2-2). The films were dried for 16 hours at 25° C., then annealed at 50° C. for 1 hour and further dried for 24 hours at 25° C. Subsequently, a piece of cotton wool was soaked in 1:1 EtOH: demineralized water and placed on the film for various timespans. After removal of the EtOH and 60 minutes recovery, the following results were obtained (a score of 1 indicates complete degradation of the film, 5 indicates no damage visible):

Ethanol Spot Test

| Sample | 30 min | 240 min |
|---|---|---|
| Test 2-1 | 3 | 3 |
| Test 2-2 | 1 | 1 |

Genotoxicity Test

| | Without S9 rat liver extract | | | | | | With S9 rat liver extract | | | | | |
|---|---|---|---|---|---|---|---|---|---|---|---|---|
| concentration | Bscl 2 | | | Rtkn | | | Bscl 2 | | | Rtkn | | |
| → | 10 | 25 | 50 | 10 | 25 | 50 | 10 | 25 | 50 | 10 | 25 | 50 |
| Ex. 2 | 1.1 | 1.2 | 1.2 | 1.2 | 1.3 | 1.2 | 1.1 | 1.1 | 1.1 | 1.1 | 1.2 | 1.1 |

The genotoxicity test results show that the crosslinker composition of Example 2 is non-genotoxic.

EXAMPLE 3

A round bottom flask equipped with a condensor was placed under a $N_2$ atmosphere and charged with ethylene imine (40.0 gram), Cardura E10P (151.5 gram) and $K_2CO_3$ (4.00 gram) and heated to 40° C., after which the mixture was stirred for 48 h at T=40° C. After filtration the excess of EI was removed in vacuo, followed by further purification via vacuum distillation, resulting in a colorless low viscous liquid.

1.35 grams of the resulting material (3-(aziridin-1-yl)-2-hydroxypropyl neodecanoate) was charged to a feeding funnel together with 2.40 grams of dimethylformamide. This mixture was fed in 15 minutes to a reaction flask equipped with a thermometer and filled with 1.00 grams of Desmodur® N 3600, 4.80 grams of DMF and 0.02 grams of bismuth neodecanoate at 50° C., while the mixture was stirred with a mechanical upper stirrer under a nitrogen atmosphere. After the feed was completed, the mixture was heated further to 80° C. Samples were taken at regular intervals and the reaction progress was monitored using a Bruker Alpha FT-IR spectrometer until no change in NCO-stretch at 2200-2300 $cm^{-1}$ was observed. Subsequently, 0.03 grams of 1-butanol were added to the mixture, followed by further reaction to complete disappearance of the aforementioned NCO-stretch peak. Concentration of the solution in vacuo to a 25 wt % solution yielded a slightly viscous liquid.

The calculated molecular weight of the theoretical main component was 1317.91 Da, chemical structure is shown below.

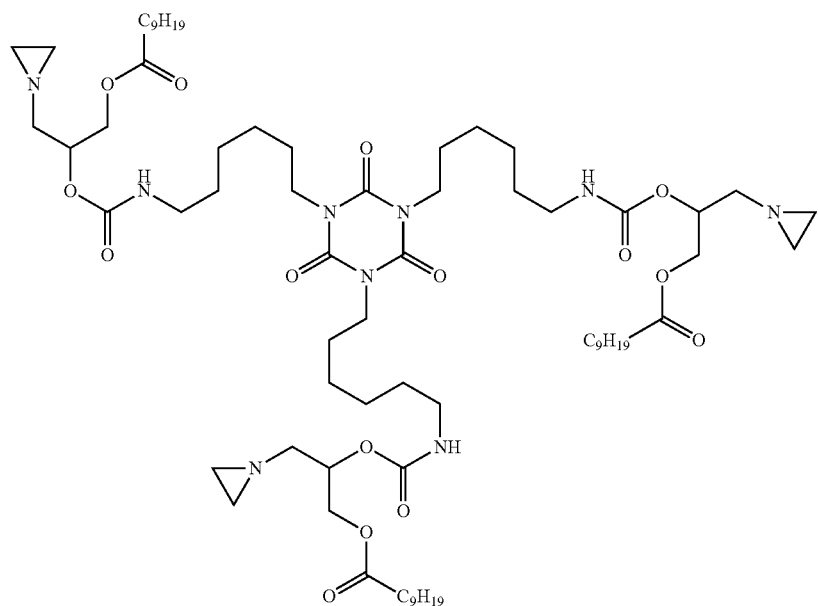

Molecular weight was confirmed by Maldi-TOF-MS: Calcd. [M+Na+]=1340.91 Da; Obs. [M+Na+]=1340.88 Da.

The following components with a mass below 820 Da were determined by LC-MS and quantified:

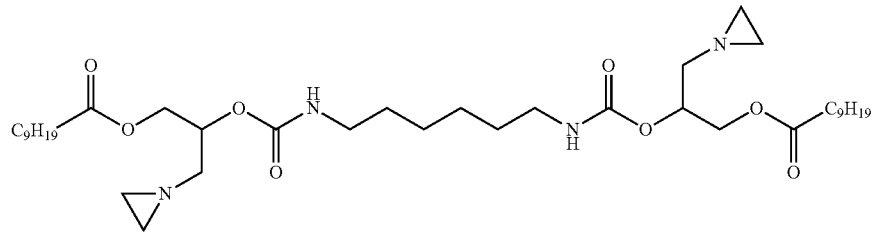

was present in the composition at less than 0.01 wt % and

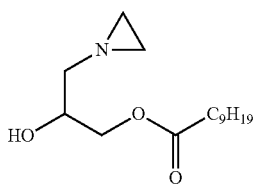

was present at 0.07 wt. %.

Performance of the synthesized compound as a crosslinker was assessed using spot tests on coating surfaces, based on procedures from the DIN 68861-1:2011-01 standard. For these tests, 2.0 parts of the crosslinker solution were added to 10 parts of P1 under continuous stirring, and the resulting mixture was further stirred for 30 minutes. Afterwards, this coating composition was filtered and applied to Leneta test cards using 100 μm wire rod applicators (Test 3-1). For reference, films were also cast from the same composition lacking a crosslinker (Test 3-2). The films were dried for 16 hours at 25° C., then annealed at 50° C. for 1 hour and further dried for 24 hours at 25° C. Subsequently, a piece of cotton wool was soaked in 1:1 EtOH: demineralized water and placed on the film for various timespans. After removal of the EtOH and 60 minutes recovery, the following results were obtained (a score of 1 indicates complete degradation of the film, 5 indicates no damage visible):

Ethanol Spot Test

| Sample | 30 min | 240 min |
|---|---|---|
| Test 3-1 | 4 | 4 |
| Test 3-2 | 1 | 1 |

Genotoxicity Test

| | Without S9 rat liver extract | | | | | | With S9 rat liver extract | | | | | |
|---|---|---|---|---|---|---|---|---|---|---|---|---|
| concentration | Bscl 2 | | | Rtkn | | | Bscl 2 | | | Rtkn | | |
| → | 10 | 25 | 50 | 10 | 25 | 50 | 10 | 25 | 50 | 10 | 25 | 50 |
| Ex. 3 | 1.1 | 1.2 | 1.4 | 1.3 | 1.5 | 1.5 | 1.1 | 1.2 | 1.2 | 1.3 | 1.5 | 1.5 |

The genotoxicity test results show that the crosslinker composition of Example 3 is non-genotoxic.

EXAMPLE 4

A round bottom flask equipped with a condensor was placed under a $N_2$ atmosphere and charged with ethylene imine (50.0 gram), n-butyl glycidyl ether (108.0 gram) and $K_2CO_3$ (5.00 gram) and heated to 40° C. in 30 min, after which the mixture was stirred for 48 h at T=40° C. After filtration the excess of EI was removed in vacuo, followed by further purification via vacuum distillation, resulting in a colorless low viscous liquid. 3.37 grams of the resulting material (1-(aziridin-1-yl)-3-butoxypropan-2-ol) was charged to a feeding funnel together with 5.4 grams Jeffamine® XTJ-436 (CAS number 118270-87-4, obtained from Huntsman) and 30 grams of dimethylformamide. This mixture was fed in 15 minutes to a reaction flask equipped with a thermometer and filled with 5.00 grams of Desmodur® N 3600, 40 grams of DMF and 0.12 grams of bismuth neodecanoate at 50° C., while the mixture was stirred with a mechanical upper stirrer under a nitrogen atmosphere. After the feed was completed, the mixture was heated further to 80° C. Samples were taken at regular intervals and the reaction progress was monitored using a Bruker Alpha FT-IR spectrometer until no change in NCO-stretch at 2200-2300 $cm^{-1}$ was observed. Subsequently, 0.16 grams of 1-butanol were added to the mixture, followed by further reaction to complete disappearance of aforementioned NCO-stretch peak. Concentration of the solution in vacuo to a 25 wt % solution yielded a slightly viscous liquid.

The calculated molecular weights of the theoretical main components were 1023.69 Da (three aziridines), 1824.30 Da (two aziridines, 13 PO repeating units) and 1882.34 Da (two aziridines, 14 PO repeating units).

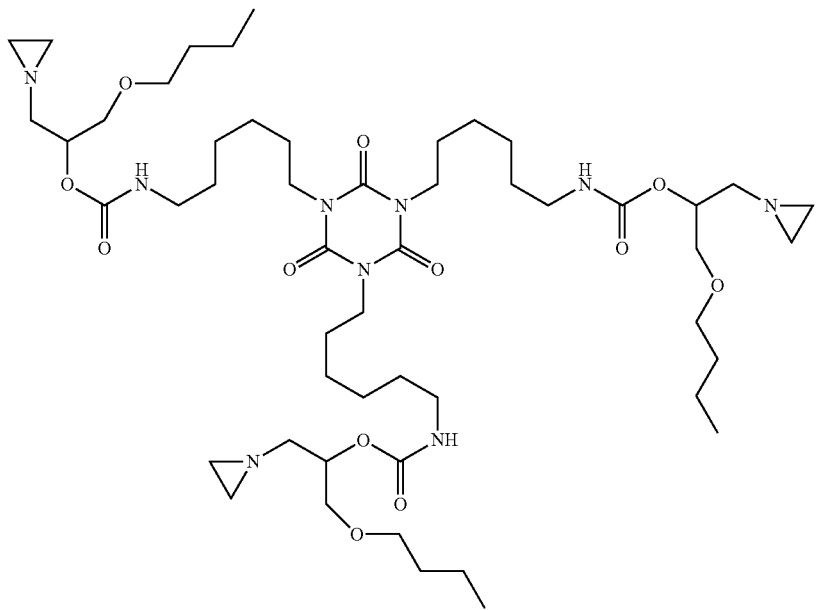

Molecular weight was confirmed by Maldi-TOF-MS: Calcd. [M+Na+]=1046.69 Da; Obs. [M+Na+]=1046.71 Da.

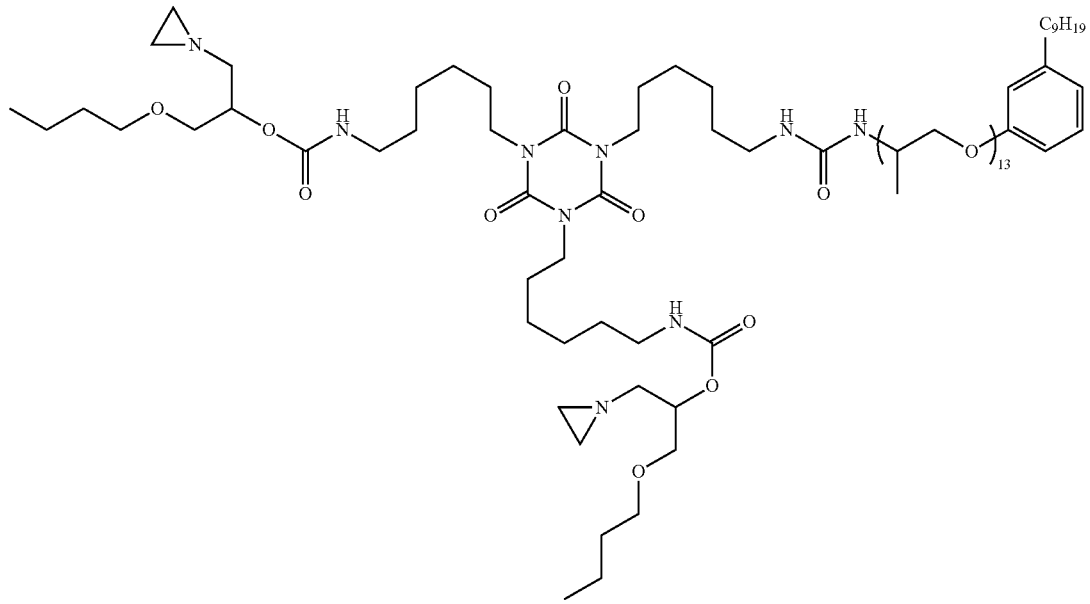

Molecular weight was confirmed by Maldi-TOF-MS: Calcd. [M+Na+]=1847.29 Da; Obs. [M+Na+]=1847.40 Da.

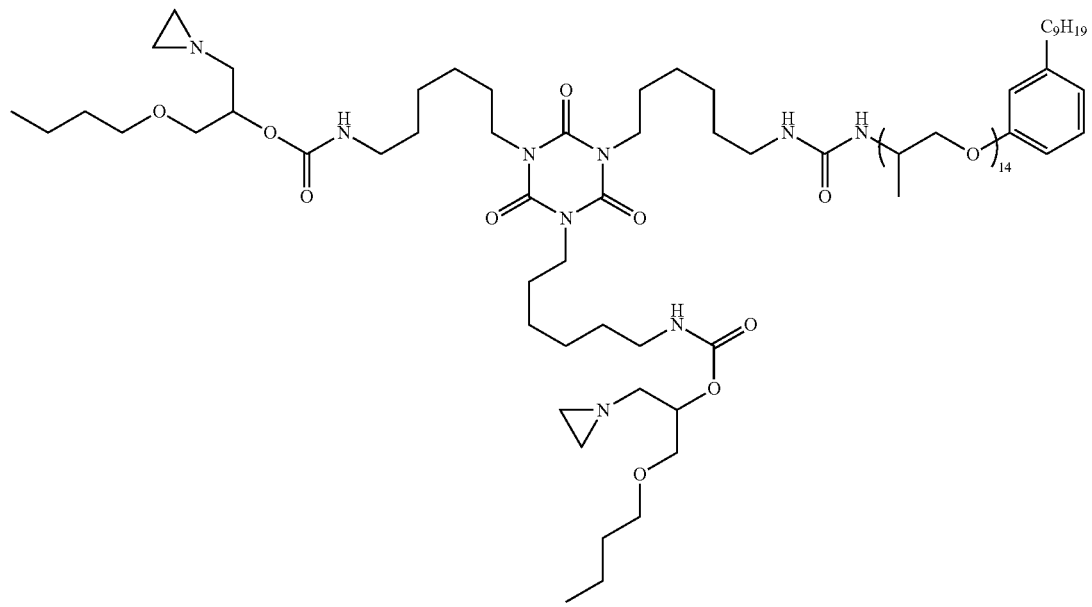

Molecular weight was confirmed by Maldi-TOF-MS: Calcd. [M+Na+]=1905.33 Da; Obs. [M+Na+]=1905.44 Da.

The following components with a mass below 820 Da were determined by LC-MS and quantified:

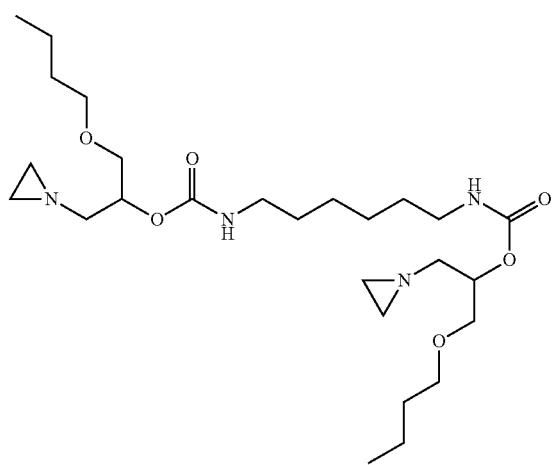 [SMILES: CCCCOCC(CN1CC1)OC(=O)NCCCCCCNC(=O)OC(COCCCC)CN1CC1]

was present in the composition at less than 0.01 wt % and

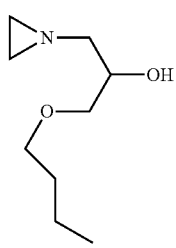

was present at less than 0.01 wt. %.

Performance of the synthesized compound as a crosslinker was assessed using spot tests on coating surfaces, based on procedures from the DIN 68861-1:2011-01 standard. For these tests, 1.0 parts of the crosslinker solution were added to 15 parts of P1 under continuous stirring, and the resulting mixture was further stirred for 30 minutes. Afterwards, this coating composition was filtered and applied to Leneta test cards using 100 μm wire rod applicators (Test 4-1). For reference, films were also cast from the same composition lacking a crosslinker (Test 4-2). The films were dried for 16 hours at 25° C., then annealed at 50° C. for 1 hour and further dried for 24 hours at 25° C. Subsequently, a piece of cotton wool was soaked in 1:1 EtOH: demineralized water and placed on the film for various timespans. After removal of the EtOH and 60 minutes recovery, the following results were obtained (a score of 1 indicates complete degradation of the film, 5 indicates no damage visible):

Ethanol Spot Test

| Sample | 60 min | 240 min |
| --- | --- | --- |
| Test 4-1 | 3 | 3 |
| Test 4-2 | 1 | 1 |

A waterborne acrylic binder was synthesized as follows.

A 2 L four-necked flask equipped with a thermometer and overhead stirrer was charged with sodium lauryl sulphate (30% solids in water, 18.6 grams of solution) and demineralized water (711 grams). The reactor phase was placed under $N_2$ atmosphere and heated to 82° C. A mixture of demineralized water (112 grams), sodium lauryl sulphate (30% solids in water, 37.2 grams of solution), methyl methacrylate (174.41 grams), n-butyl acrylate (488.44 grams) and methacrylic acid (34.88 grams) was placed in a large feeding funnel and emulsified with an overhead stirrer (monomer feed). Ammonium persulphate (1.75 grams) was dissolved in demineralized water (89.61 grams) and placed in a small feeding funnel (initiator feed). Ammonium persulphate (1.75 grams) was dissolved in demineralized water (10.5 grams), and this solution was added to the reactor phase. Immediately afterwards, 5% by volume of the monomer feed was added to the reactor phase. The reaction mixture then exothermed to 85° C. and was kept at 85° C. for 5 minutes. Then, the residual monomer feed and the initiator feed were fed to the reaction mixture over 90 minutes, maintaining a temperature of 85° C. After completion of the feeds, the monomer feed funnel was rinsed with demineralized water (18.9 grams) and reaction temperature maintained at 85° C. for 45 minutes. Subsequently, the mixture was cooled to room temperature and brought to pH=7.2 with ammonia solution (6.25 wt. % in demineralized water), and brought to 40% solids with further demineralized water.

For further spot tests, performance of the synthesized compound as a crosslinker was assessed using spot tests on coating surfaces, based on procedures from the DIN 68861-1:2011-01 standard. For these tests, 1.1 parts of the crosslinker solution were added to 15 parts of the acrylic binder described above under continuous stirring, and the resulting mixture was further stirred for 30 minutes. Afterwards, this coating composition was filtered and applied to Leneta test cards using 100 μm wire rod applicators (Test 4-3). For reference, films were also cast from the same composition lacking a crosslinker (Test 4-4). The films were dried for 16 hours at 25° C., then annealed at 50° C. for 1 hour and further dried for 24 hours at 25° C. Subsequently, a piece of cotton wool was soaked in 1:1 EtOH: demineralized water and placed on the film for various timespans. After removal of the EtOH and 60 minutes recovery, the following results were obtained (a score of 1 indicates complete degradation of the film, 5 indicates no damage visible):

Ethanol Spot Test

| Sample | 60 min | 240 min |
|--------|--------|---------|
| Test 4-3 | 3 | 3 |
| Test 4-4 | 1 | 1 |

Genotoxicity Test

| concentration → | Without S9 rat liver extract | | | | | | With S9 rat liver extract | | | | | |
|---|---|---|---|---|---|---|---|---|---|---|---|---|
| | Bscl 2 | | | Rtkn | | | Bscl 2 | | | Rtkn | | |
| | 10 | 25 | 50 | 10 | 25 | 50 | 10 | 25 | 50 | 10 | 25 | 50 |
| Ex. 4 | 1.0 | 1.0 | 1.1 | 1.0 | 1.1 | 1.1 | 1.0 | 1.0 | 1.0 | 1.0 | 1.0 | 1.0 |

The genotoxicity test results show that the crosslinker composition of Example 4 is non-genotoxic.

EXAMPLE 5

A round bottom flask equipped with a condenser was placed under a $N_2$ atmosphere and charged with ethylene imine (50.0 gram), n-butyl glycidyl ether (108.0 gram) and $K_2CO_3$ (5.00 gram) and heated to 40° C. in 30 min, after which the mixture was stirred for 48 h at T=40° C. After filtration the excess of EI was removed in vacuo, followed by further purification via vacuum distillation, resulting in a colorless low viscous liquid. 5.61 grams of the resulting material (1-(aziridin-1-yl)-3-butoxypropan-2-ol) was charged to a reaction flask equipped with a thermometer, together with 0.02 grams of bismuth neodecanoate and 32 grams of dimethylformamide. The mixture was stirred with a mechanical upper stirrer under a nitrogen atmosphere and heated to 50° C. A solution of 6.30 grams of Desmodur® N 3900 in 34 grams of dimethylformamide was then added dropwise in 15 minutes to the reaction flask, while keeping the reaction temperature constant at 50° C. Samples were taken at regular intervals and the reaction progress was monitored using a Bruker Alpha FT-IR spectrometer until no change in NCO-stretch at 2200-2300 $cm^{-1}$ was observed. Subsequently, 0.21 grams of 1-butanol were added to the mixture, followed by further reaction to complete disappearance of aforementioned NCO-stretch peak. Concentration of the solution in vacuo to a 25 wt % solution yielded a slightly viscous liquid.

The calculated theoretical molecular weight of the main component was 1023.69 Da, chemical structure is shown below.

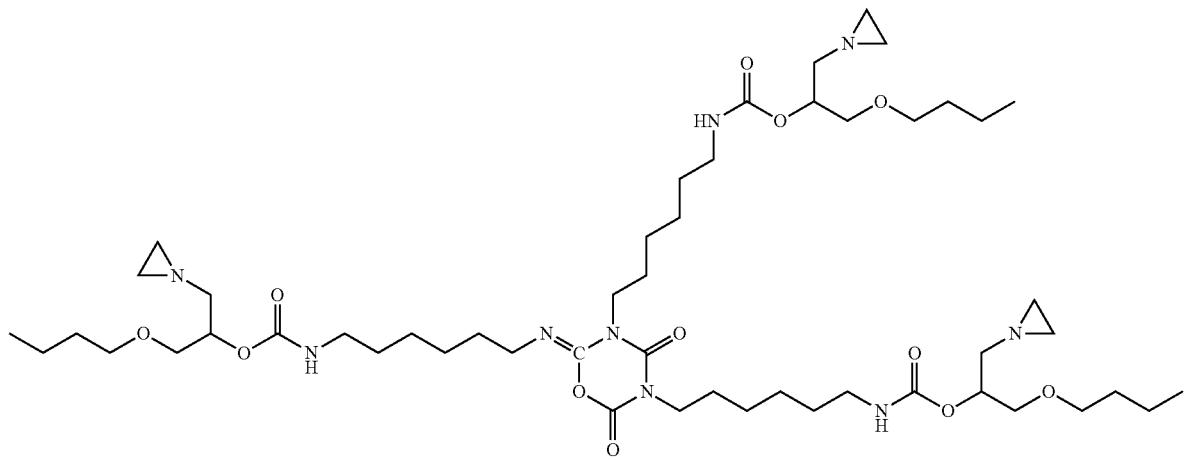 [SMILES: CCCCOCC(CN1CC1)OC(=O)NCCCCCC/N=c1\oc(=O)n(CCCCCCNC(=O)OC(COCCCC)CN2CC2)c(=O)n1CCCCCCNC(=O)OC(COCCCC)CN1CC1]

Molecular weight was confirmed by Maldi-TOF-MS: Calcd. [M+Na+]=1046.69 Da; Obs. [M+Na+]=1046.73 Da.

The following components with a mass below 820 Da were determined by LC-MS and quantified:

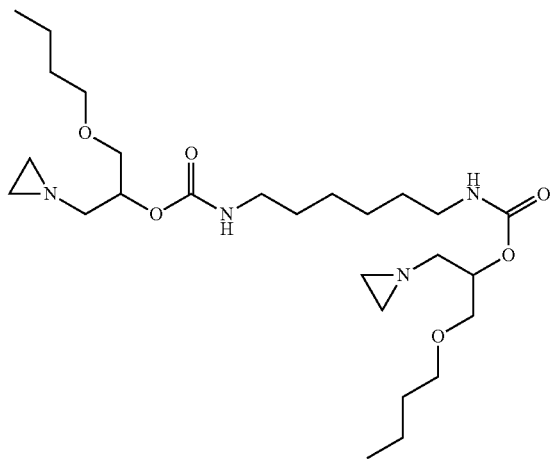 [SMILES: CCCCOCC(CN1CC1)OC(=O)NCCCCCCNC(=O)OC(COCCCC)CN1CC1]

was present in the composition at 0.07 wt % and

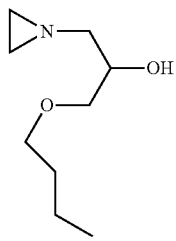

was present at less than 0.01 wt. % and

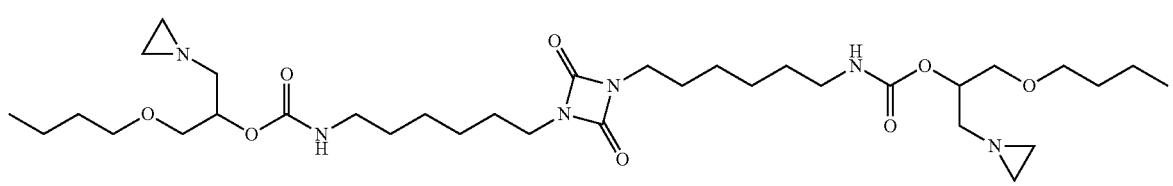 [SMILES: CCCCOCC(CN1CC1)OC(=O)NCCCCCCN1C(=O)N(CCCCCCNC(=O)OC(COCCCC)CN2CC2)C1=O]

was present at less than 0.01 wt. %.

Performance of the synthesized compound as a crosslinker was assessed using spot tests on coating surfaces, based on procedures from DIN 68861-1:2011-01 standard. For these tests, 1.4 parts of the crosslinker solution were added to 10 parts of P1 under continuous stirring, and the resulting mixture was further stirred for 30 minutes. Afterwards, this coating composition was filtered and applied to Leneta test cards using 100 μm wire rod applicators (Test 5-1). For reference, films were also cast from the same composition lacking a crosslinker (Test 5-2). The films were dried for 16 hours at 25° C., then annealed at 50° C. for 1 hour and further dried for 24 hours at 25° C. Subsequently, a piece of cotton wool was soaked in 1:1 EtOH: demineralized water and placed on the film for various timespans. After removal of the EtOH and 60 minutes recovery, the following results were obtained (a score of 1 indicates complete degradation of the film, 5 indicates no damage visible):

Ethanol Spot Test

| Sample | 60 min | 240 min |
|---|---|---|
| Test 5-1 | 5 | 4 |
| Test 5-2 | 1 | 1 |

Genotoxicity Test

| | Without S9 rat liver extract | | | | | | With S9 rat liver extract | | | | | |
|---|---|---|---|---|---|---|---|---|---|---|---|---|
| | Bscl 2 | | | Rtkn | | | Bscl 2 | | | Rtkn | | |
| concentration → | 10 | 25 | 50 | 10 | 25 | 50 | 10 | 25 | 50 | 10 | 25 | 50 |
| Ex. 5 | 1.1 | 1.1 | 0.9 | 1.0 | 1.1 | 1.0 | 1.1 | 1.1 | 1.2 | 1.0 | 0.9 | 1.0 |

The genotoxicity test results show that the crosslinker composition of example 5 is non-genotoxic.

COMPARATIVE EXAMPLE 5

Comparative Example 5 is pentaerythritol tris(3-(1-aziridinyl)propionate), CAS number 57116-45-7, obtained from ABCR. Chemical structure is shown below.

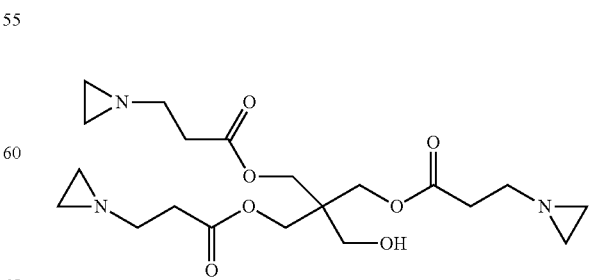

Genotoxicity Test

| concentration → | Without S9 rat liver extract | | | | | | With S9 rat liver extract | | | | | |
|---|---|---|---|---|---|---|---|---|---|---|---|---|
| | Bscl 2 | | | Rtkn | | | Bscl 2 | | | Rtkn | | |
| | 10 | 25 | 50 | 10 | 25 | 50 | 10 | 25 | 50 | 10 | 25 | 50 |
| Ex. 5 | 1.2 | 1.4 | 2.1 | 1.2 | 1.7 | 3.5 | 1.1 | 1.5 | 2.3 | 1.3 | 2.1 | 4.3 |

The genotoxicity test results show that the crosslinker of Comp Ex 5 is genotoxic.

The invention claimed is:

1. A multi-aziridine compound having:
a) from 2 to 6 of the following structural units (A):

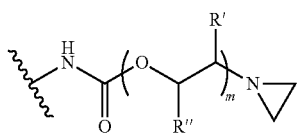

(A)

whereby
m is an integer from 1 to 6; and
R' and R" are according to (1) or (2):
(1) R'=H or an aliphatic hydrocarbon group containing from 1 to 14 carbon atoms,
R"=a cycloaliphatic hydrocarbon group containing from 5 to 12 carbon atoms, an aromatic hydrocarbon group containing from 6 to 12 carbon atoms, CH$_2$—O—(C=O)—R''', CH$_2$—O—R'''', or CH$_2$—(OCR''''HCR''''H)$_n$—OR''''', whereby R''' is an aliphatic hydrocarbon group containing from 1 to 14 carbon atoms and R'''' is an aliphatic hydrocarbon group containing from 1 to 14 carbon atoms or an aromatic hydrocarbon group containing from 6 to 12 carbon atoms, n being from 1 to 35, R'''''' independently being H or an aliphatic hydrocarbon group containing from 1 to 14 carbon atoms and R''''' being an aliphatic hydrocarbon group containing from 1 to 4 carbon atoms, and
(2) R' and R" form together a saturated cycloaliphatic hydrocarbon group containing from 5 to 8 carbon atoms;
b) one or more linking chains wherein each one of these linking chains links two of the structural units A, whereby a linking chain is the shortest chain of consecutive atoms that links two structural units A; and
c) a molecular weight in the range from 840 Daltons to 5000 Daltons, wherein the molecular weight is determined using MALDI-TOF mass spectrometry.

2. The multi-aziridine compound according to claim 1, wherein
m is 1;
R' and R" are according to (1) or (2):
(1) R'=H or an alkyl group containing from 1 to 2 carbon atoms, and
R"=CH$_2$—O—(C=O)—R''', CH$_2$—O—R'''', or CH$_2$—(OCR''''HCR''''H)$_n$—OR''''', whereby R''' is an alkyl group containing from 1 to 14 carbon atoms and R'''' is an alkyl group containing from 1 to 14 carbon atoms, n being from 1 to 35, R'''''' independently being H or a methyl group and R''''' being an alkyl group containing from 1 to 4 carbon atoms, and;

(2) R' and R" form part of a saturated cycloaliphatic hydrocarbon group containing from 5 to 8 carbon atoms.

3. The multi-aziridine compound according to claim 1, wherein
R'=H, and
R"=a cycloaliphatic hydrocarbon group containing from 5 to 12 carbon atoms, an aromatic hydrocarbon group containing from 6 to 12 carbon atoms, CH$_2$—O—(C=O)—R''', CH$_2$—O—R'''', or CH$_2$—(OCR''''HCR''''H)$_n$—OR''''', whereby R''' is an aliphatic hydrocarbon group containing from 1 to 14 carbon atoms and R'''' is an aliphatic hydrocarbon group containing from 1 to 14 carbon atoms or an aromatic hydrocarbon group containing from 6 to 12 carbon atoms, n being from 1 to 35, R'''''' independently being H or an aliphatic hydrocarbon group containing from 1 to 14 carbon atoms and R''''' being an aliphatic hydrocarbon group containing from 1 to 4 carbon atoms.

4. The multi-aziridine compound according to claim 1, wherein R' is
H and R"=CH$_2$—O—(C=O)—R''', CH$_2$—O—R'''', or CH$_2$—(OCH$_2$CH$_2$)$_n$—OCH$_3$, whereby R''' is an alkyl group containing from 3 to 12 carbon atoms and R'''' is an alkyl group containing from 1 to 14 carbon atoms.

5. The multi-aziridine compound according to claim 1, wherein the multi-aziridine compound contains 2 or 3 structural units (A).

6. The multi-aziridine compound according to claim 1, wherein the linking chains consist of from 4 to 300 atoms and the linking chains are a collection of atoms covalently connected which collection of atoms consists of i) carbon atoms, ii) carbon and nitrogen atoms, or iii) carbon, oxygen and nitrogen atoms.

7. The multi-aziridine compound according to claim 1, wherein the multi-aziridine compound has a molecular weight of from 840 to 3800 Daltons, whereby the molecular weight is determined using MALDI-TOF mass spectrometry.

8. The multi-aziridine compound according to claim 1, wherein the multi-aziridine compound comprises one or more connecting groups wherein each one of these connecting groups connects two of the structural units A, whereby the connecting groups consist of at least one functionality selected from:
aliphatic hydrocarbon functionality, cycloaliphatic hydrocarbon functionality, aromatic hydrocarbon functionality, isocyanurate functionality, iminooxadiazindione functionality, ether functionality, ester functionality, amide functionality, carbonate functionality, urethane functionality, urea functionality, biuret functionality, allophanate functionality, uretdione functionality and any combination thereof.

9. The multi-aziridine compound according to claim 8, wherein the connecting groups of the multi-aziridine compound consist of at least one functionality selected from:
aliphatic hydrocarbon functionality, cycloaliphatic hydrocarbon functionality, aromatic hydrocarbon functionality, isocyanurate functionality, iminooxadiazindione functionality, urethane functionality, urea functionality, biuret functionality and any combination thereof.

10. The multi-aziridine compound according to claim 1, wherein the multi-aziridine compound comprises one or more connecting groups wherein each one of these connecting groups connects two of the structural units A, wherein the connecting groups consist of (i) at least two aliphatic hydrocarbon functionality or at least two cycloaliphatic hydrocarbon functionality and (ii) an isocyanurate functionality or an iminooxadiazindione functionality, and wherein a pendant group is present on a connecting group, whereby the pendant group has the following structural formula:

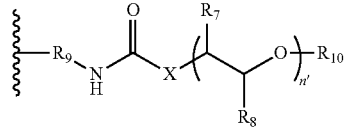

n' is the number of repeating units and is an integer from 1 to 50,

X is O or NH, $R_7$ and $R_8$ are independently H or $CH_3$ in each repeating unit, $R_9$ is an aliphatic hydrocarbon group or a cycloaliphatic hydrocarbon group and $R_{10}$ contains at most 20 carbon atoms and is an aliphatic, cycloaliphatic or aromatic hydrocarbon group or a combination thereof.

11. The multi-aziridine compound according to claim 10, wherein X is O and $R_7$ and $R_8$ are H.

12. The multi-aziridine compound according to claim 10, wherein the multi-aziridine compound contains 2 structural units (A).

13. The multi-aziridine compound according to claim 12, wherein the connecting group consists of the array of the following consecutive functionalities: a first aliphatic hydrocarbon functionality, an isocyanurate functionality or an iminooxadiazindione functionality, and a second aliphatic hydrocarbon functionality, and $R_9$ is an aliphatic hydrocarbon group, whereby the first and second aliphatic hydrocarbon functionality and $R_9$ are identical.

14. The multi-aziridine compound according to claim 1, wherein the multi-aziridine compound contains polyoxyethylene (—O—CH2-CH2-)$_x$ group(s) in an amount of at least 0.1 wt. % and in an amount of less than 45 wt. % relative to the multi-aziridine compound.

15. The multi-aziridine compound according to claim 1, wherein the multi-aziridine compound is obtained by reacting at least a polyisocyanate and a compound B with the following structural formula:

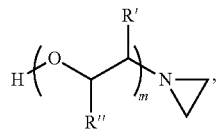

whereby the molar ratio of compound B to polyisocyanate is from 2 to 6.

16. The multi-aziridine compound according to claim 15, wherein the polyisocyanate is a polyisocyanate with aliphatic reactivity that is a compound in which all of the isocyanate groups are directly bonded to aliphatic or cycloaliphatic hydrocarbon groups, irrespective of whether aromatic hydrocarbon groups are also present.

17. The multi-aziridine compound according to claim 15, wherein compound B is obtained by reacting at least a non-OH functional monoepoxide compound with ethyleneimine.

18. The multi-aziridine compound according to claim 17, wherein the non-OH functional monoepoxide compound is selected from the group consisting of n-butylglycidylether, 2-ethylhexylglycidylether, glycidyl neodecanoate, and any mixture thereof.

19. A crosslinker composition comprising at least one multi-aziridine compound according to claim 1 and further comprising at least one additional component.

20. The crosslinker composition according to claim 19, wherein the amount of aziridine functional molecules having a molecular weight lower than 820 Daltons is lower than 1.5 wt. % relative to the total weight of the crosslinker composition, whereby the molecular weight is determined using LC-MS.

21. The crosslinker composition according to claim 19, wherein the crosslinker composition contains less than 5 wt. % of water.

22. A two-component coating system comprising a first component and a second component each of which is separate and distinct from each other and wherein the first component comprises a carboxylic acid functional polymer dissolved and/or dispersed in an aqueous medium, whereby the carboxylic acid functional polymer contains carboxylic acid groups and/or carboxylate groups and the second component comprises a multi-aziridine compound according to claim 1.

* * * * *